(12) United States Patent
Hui

(10) Patent No.: US 7,169,907 B2
(45) Date of Patent: Jan. 30, 2007

(54) DERIVATIVES, IMMUNOGENS, AND ANTIBODIES FOR DETECTING ECSTASY-CLASS DRUGS

(75) Inventor: Raymond A. Hui, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 478 days.

(21) Appl. No.: 10/087,469

(22) Filed: Mar. 1, 2002

(65) Prior Publication Data

US 2003/0175995 A1    Sep. 18, 2003

(51) Int. Cl.
  *C07K 17/02* (2006.01)
  *C07K 16/44* (2006.01)
  *C07D 317/48* (2006.01)
  *C07D 405/12* (2006.01)
  *G01N 33/532* (2006.01)

(52) U.S. Cl. ............ 530/405; 435/7.9; 435/7.92; 436/544; 436/545; 436/546; 548/526; 549/440; 549/443; 549/444; 530/388.9; 530/389.8; 530/406

(58) Field of Classification Search ........ 549/440, 549/443, 444; 548/526; 530/389.8, 404, 530/388.9, 405, 406; 435/7.9, 7.92; 436/544, 436/545, 546

See application file for complete search history.

(56) References Cited

U.S. PATENT DOCUMENTS

| | | | |
|---|---|---|---|
| 3,878,187 A | | 4/1975 | Schneider et al. |
| 4,067,774 A | * | 1/1978 | Rubenstein et al. ........ 435/188 |
| 4,868,132 A | | 9/1989 | Byrnes et al. |
| 5,101,015 A | | 3/1992 | Brynes et al. |
| 5,135,863 A | | 8/1992 | Hu et al. |
| 5,262,333 A | | 11/1993 | Heiman et al. |
| 5,976,812 A | | 11/1999 | Huber et al. |
| 6,669,937 B1 | * | 12/2003 | Owens et al. ............ 424/142.1 |
| 2003/0207469 A1 | * | 11/2003 | Rouhani et al. ............ 436/518 |
| 2004/0121400 A1 | * | 6/2004 | McConnell et al. ......... 435/7.1 |

FOREIGN PATENT DOCUMENTS

| | | |
|---|---|---|
| DE | 198 57 196 | 6/2000 |
| EP | 0 399 184 | 11/1990 |
| GB | 2 361 473 | 10/2001 |
| WO | WO 00/36423 | 6/2000 |

OTHER PUBLICATIONS

U. Braun et al, J. Pharmaceutical Sciences (1980), vol. 69, No. 2, pp. 192-195.*
Bob T. Ramage, Jeff E. Shindelman, Mike Leos, Riaz Rhouhani, Rao Kammula, William A. Coty, Yuh-Geng Tsay. "CEDIA® Ecstasy Drugs Assay for Urine Drug Testing"; SOFT Meeting, Poster No. 34, Oct. 2000, one page.
Product pamphlet for Microgenics Ecstasy Drug Screen Assay, Jul. 2001, 2 pages.
Product pamphlet for Microgenics Amphetamines/Ecstasy Assay, Jul. 2001, 2 pages.

* cited by examiner

*Primary Examiner*—Mary E. Ceperley
(74) *Attorney, Agent, or Firm*—Marilyn L. Amick; Roche Diagnostics Operations, Inc.

(57) ABSTRACT

Compounds including haptens, intermediates, and immunogens that are useful in the production of antibodies specific for the methylenedioxy class of amphetamine derivatives are described. Antibodies specific for the methylenedioxy class of amphetamine derivatives, reagent kits containing antibodies specific for the methylenedioxy class of amphetamine derivatives, methods of producing antibodies specific for the methylenedioxy class of amphetamine derivatives, and methods of detecting analytes including members of the methylenedioxy class of amphetamine derivatives are also described.

18 Claims, 8 Drawing Sheets

FIG. 4

Fusion 1 and 2
1) Immunogen 12 (T = KLH, 12a), classical regimen
2) $3.7 \times 10^8$ lymphocytes total
3) Fusion 1 = R0 myeloma, Fusion 2 = P3 myeloma, 47 plates each
4) Screened on MDMA-BSA 12 (T = BSA, 12b) (in the presence and absence of free MDMA, MDEA, and pseudoephedrine), Amp-BSA 30, and MAMP-BSA 28

Fusion 3 (11 weeks later)
1) Immunogen 12 (T = KLH), deprotected, classical regimen
2) $1.45 \times 10^8$ lymphocytes, 36 plates
3) 12 selected from 1,979 wells tested, same testing protocol as in Fusions 1 and 2.

Table 1

| Clone | OD$_{450}$ using 12b-coated plates | | | | OD$_{450}$ using plates coated with | | Percent Cross-Reactivity | | | | | | | | | | | | | | | |
|---|---|---|---|---|---|---|---|---|---|---|---|---|---|---|---|---|---|---|---|---|---|---|
| | 12b alone | In the presence of | | | 30 Amp | 28 MAMP | MDMA | MDEA | MDA | MBDB | BDB | MDPA | dAM | dMA | IAM | 1MA | Ses | Phen | Tyr pseu | Eph eph | PPA PPA | Adr Ephdr | Ran |
| | | MDMA | MDEA | Pseu | | | | | | | | | | | | | | | | | | |
| 1 | 1.051 | 0.611 | 0.227 | 1.076 | 0.134 | 0.169 | | | | | | | | | | | | | | | | |
| 1.1 | 3.946 | 2.713 | 1.539 | 4.138 | 0.109 | 0.183 | | | | | | | | | | | | | | | | |
| 1.2 | 4.123 | 4.036 | 4.036 | 4.148 | 0.160 | 0.235 | | | | | | | | | | | | | | | | |
| 1.3 | 4.200 | 3.941 | 4.200 | 4.200 | 0.149 | 0.232 | | | | | | | | | | | | | | | | |
| 2 | 3.169 | - | - | - | - | - | | | | | | | | | | | | | | | | |
| 2.1 | 3.771 | 0.796 | 0.370 | 3.806 | 0.139 | 0.153 | 100 | 204 | 60.6 | 26.1 | 20.5 | 365 | 0 | 0.65 | | 0 | 0 | 0 | 0 | 0 | 0 | 0 |
| 2.1.1 | 4.200 | 0.857 | 0.754 | 3.910 | 1.679 | 0.089 | | | | | | | | | | | | | | | | |
| 2.1.2 | 4.200 | 0.667 | 0.313 | 3.929 | 0.253 | 0.247 | | | | | | | | | | | | | | | | |
| 2.1.3 | 4.200 | 0.721 | 0.346 | 3.794 | 0.245 | 0.161 | | | | | | | | | | | | | | | | |
| 2.1.4 | 4.162 | 0.649 | 0.293 | 3.969 | 0.092 | 0.091 | | | | | | | | | | | | | | | | |
| 2.1.5 | 4.003 | 0.545 | 0.385 | 4.056 | 0.099 | 0.080 | 100 | 241 | 105 | 26.6 | 23.6 | 366 | 0 | 0 | 0 | 0 | 0 | 0 | 0 | 0 | 0 | 0 |
| 2.1.6 | 3.885 | 0.778 | 0.400 | 3.982 | 1.205 | 0.144 | 100 | 137 | 54.7 | 15.3 | 11.8 | 812 | 0 | 0.59 | 0 | 0 | 1.07 | 0 | 0 | 0 | 0 | 0 |
| 3 | 1.035 | - | - | - | - | - | | | | | | | | | | | | | | | | |
| 4 | 1.399 | - | - | - | - | - | | | | | | | | | | | | | | | | |
| 4.1 | 0.736 | 1.384 | 1.363 | 1.303 | 0.685 | 0.236 | | | | | | | | | | | | | | | | |

MDMA 2.1.1 Cross-Reactivity in Modified Roche OnLine Format

MDMA calibrators

|    | [MDMA] ng/mL | Rate  |
|----|--------------|-------|
| S1 | 0            | 15842 |
| S2 | 250          | 12977 |
| S3 | 500          | 10996 |
| S4 | 1000         | 9434  |
| S5 | 3000         | 8043  |

Span Data

|       |      |        |
|-------|------|--------|
| S1-S2 | 2866 | 36.74% |
| S2-S3 | 1981 | 25.40% |
| S3-S4 | 1562 | 20.02% |
| S4-S5 | 1391 | 17.84% |
| Total | 7799 |        |

| Drug        | Amount spiked ng/mL | Instrument reading | % CR  |
|-------------|---------------------|--------------------|-------|
| d-MAMP      | 625                 | 0                  | 0     |
| d-AMP       | 625                 | 0                  | 0     |
| MDMA        | 625                 | 714                | 114.2 |
| MDEA        | 625                 | 1864               | 298.2 |
| BDB         | 5000                | 195                | 3.9   |
| MBDB        | 5000                | 625                | 12.5  |
| PPA         | 200000              | 0                  | 0     |
| Phent       | 200000              | 0                  | 0     |
| Phendim     | 200000              | 0                  | 0     |
| Tyramine    | 200000              | 0                  | 0     |
| l-eph       | 200000              | 0                  | 0     |
| d-pseudoeph | 200000              | 0                  | 0     |
| l-AMP       | 200000              | 0                  | 0     |
| l-MAMP      | 200000              | 170                | 0.09  |

Calibration curve

DERIVATIVES, IMMUNOGENS, AND ANTIBODIES FOR DETECTING ECSTASY-CLASS DRUGS

RELATED APPLICATIONS

The co-pending and commonly assigned U.S. patent application Ser. No. 10/087,612 for "Compounds, Antibodies, Reagent Kits, Methods of Producing Antibodies, and Methods of Detecting Analytes" was filed on the same day as the present application and is incorporated herein by reference in its entirety.

BACKGROUND

The present invention relates to immunoassays, more particularly, to immunoassays for derivatives of amphetamine, and especially to "ecstasy drugs."

The use and abuse of a class of illicit designer drugs known commonly as "ecstasy drugs" have increased significantly in recent years. These compounds, which are derivatives of amphetamine distinguished by having a fused methylenedioxy-phenyl ring system, include: MDA (3,4-methylenedioxyamphetamine); MDMA also known as "Ecstasy" (3,4-methylenedioxy-N-methylamphetamine); MDEA also known as "Eve" (3,4-methylenedioxy-N-ethylamphetamine); BDB (3,4-methylenedioxyphenyl-2-butanamine); MBDB (3,4-methylenedioxyphenyl-N-methylbutanamine); and MDPA (3,4-methylenedioxy-N-propylamphetamine).

Heretofore, methods for the detection of ecstasy drugs have primarily involved immunoassays originally developed for the detection of amphetamine and/or methamphetamine. The detection of an ecstasy drug by such assays relies on the limited cross-reactivities that may coincidentally exist between the ecstasy drug and the amphetamine and/or methamphetamine antibodies. A positive result obtained by such an assay may still not indicate which particular substance or member of the methylenedioxy class of derivatives is present in a sample.

In general, amphetamine and methamphetamine immunoassays are relatively insensitive to and non-specific for ecstasy drugs. Such assays show particularly limited recognition for the MDEA ("Eve") derivative.

The present invention is directed to remedying these and other problems relating to the use of conventional amphetamine and/or methamphetamine immunoassays for the detection of members of the methylenedioxy (MD) class of ecstasy drugs.

SUMMARY

The scope of the present invention is defined solely by the appended claims, and is not affected to any degree by the statements within this summary.

Briefly stated, a compound embodying features of the present invention has a structure

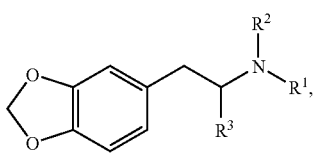

wherein $R^1$ is —J—M—T; $R^2$ is selected from the group consisting of hydrogen, an alkyl group, and a protecting group; and $R^3$ is an optionally substituted alkyl group. J comprises 1–15 carbon atoms and 0–6 heteroatoms. M is selected from the group consisting of —O—, —CO—, —NR$^4$—, —S—, —C(=NH)O—, —NH(CO)—, —NH(CO)NH—, —NH(CS)—, —NH(CS)NH—, —O(CO)NH—, —NH(C=NH)—, and maleimidothioether, wherein $R^4$ is selected from the group consisting of hydrogen and an alkyl group. T is selected from the group consisting of hydrogen, a hydroxyl, a leaving group, a macromolecular carrier, and a label. $R^1$ is not —CH$_2$CN, —CH$_2$C=CH$_2$, —CHO, —CH$_2$CH$_2$OH, —CH$_2$CH$_2$OCH$_3$, or —CH$_2$CCH when $R^2$ is hydrogen and when $R^3$ is methyl.

A first antibody embodying features of the present invention is specific for an ecstasy drug.

A second antibody embodying features of the present invention is specific for an analyte having a structure

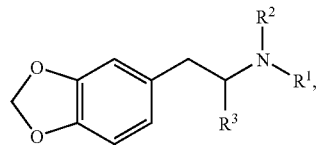

wherein $R^1$ is —J—M—T; $R^2$ is selected from the group consisting of hydrogen, an alkyl group, and a protecting group; and $R^3$ is an optionally substituted alkyl group. J comprises 1–15 carbon atoms and 0–6 heteroatoms. M is selected from the group consisting of —O—, —CO—, —NR$^4$—, —S—, —C(=NH)O—, —NH(CO)—, —NH(CO)NH—, —NH(CS)—, —NH(CS)NH—, —O(CO)NH—, —NH(C=NH)—, and maleimidothioether, wherein $R^4$ is selected from the group consisting of hydrogen and an alkyl group. T is selected from the group consisting of hydrogen, a hydroxyl, a leaving group, a macromolecular carrier, and a label.

A reagent kit embodying features of the present invention includes an antibody of a type described above.

A method of producing an antibody embodying features of the present invention includes inoculating a host with an immunogen comprising a structure

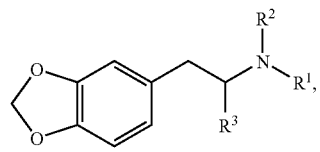

wherein $R^1$ is —J—M—T; $R^2$ is selected from the group consisting of hydrogen, an alkyl group, and a protecting group; and $R^3$ is an optionally substituted alkyl group. J comprises 1–15 carbon atoms and 0–6 heteroatoms. M is selected from the group consisting of —O—, —CO—, —NR$^4$—, —S—, —C(=NH)O—, —NH(CO)—, —NH(CO)NH—, —NH(CS)—, —NH(CS)NH—, —O(CO)NH—, —NH(C=NH)—, and maleimidothioether, wherein $R^4$ is selected from the group consisting of hydrogen and an alkyl group. T is a macromolecular carrier.

A method for detecting an analyte in a sample that embodies features of the present invention includes contacting the sample with an antibody specific for an ecstasy drug, binding the antibody to the analyte, and detecting an adduct formed by the antibody and the analyte.

BRIEF DESCRIPTION OF THE DRAWINGS

FIG. 4 shows a table of cross-reactivity data for antibodies embodying features of the present invention.

DETAILED DESCRIPTION OF THE PRESENTLY PREFERRED EMBODIMENTS

Figure 1:
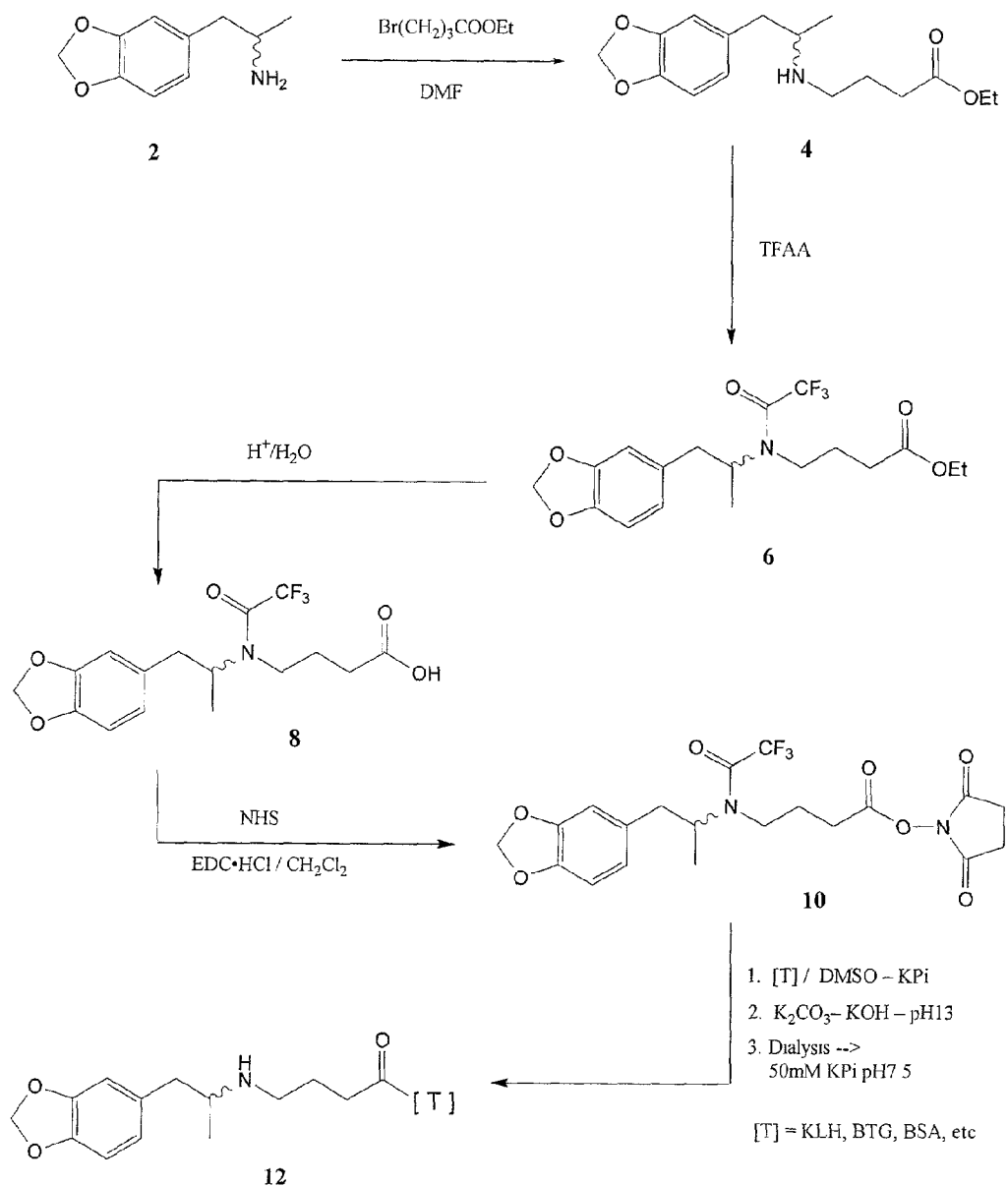
FIG. 1 shows a first representative scheme for synthesizing compounds and immunogens embodying features of the present invention.

Compounds (e.g., haptens, intermediates) and immunogens useful in the production of antibodies specific for the MD class of amphetamine derivatives, antibodies specific for the MD class of amphetamine derivatives, reagent kits containing antibodies specific for the MD class of amphetamine derivatives, methods of producing antibodies specific for the MD class of amphetamine derivatives, and methods of detecting analytes including members of the MD class of amphetamine derivatives (i.e., ecstasy drugs) have been discovered and are described hereinbelow.

Throughout this description and in the appended claims, the following definitions are to be understood: The term "immunogen" refers to any substance capable of eliciting an immune response in an organism.

The term "conjugate" refers to any substance formed from the joining together of two parts. Representative conjugates in accordance with the present invention include those formed by the joining together of a small molecule and a large molecule, such as a protein. The term "conjugate" subsumes the term "immunogen."

The term "hapten" refers to a portion of an immunogen that is typically low in molecular weight, which does not by itself stimulate antibody development.

The phrase "activated hapten" refers to a hapten that has been provided with an available reaction site—for example, by the attachment of a linking group carrying a reactive moiety—that can be used to connect the hapten to a carrier, immunogen, label, tracer, or other moiety.

The term "linking group" (or "linker") refers to a chemical moiety that is used to connect a hapten to a macromolecular carrier, immunogen, label, tracer or other moiety. The use of a linking group may or may not be advantageous or needed, depending on the specific hapten and carrier and desired specificity of antibody. Suitable linkers include straight, branched, saturated or unsaturated carbon chains, which may incorporate one or more heteroatoms—that is, atoms other than carbon (e.g., oxygen, nitrogen, sulfur, etc.)—within the chain or substituted onto and/or at a terminus thereof.

The phrases "carrier" and "macromolecular carrier" refer to high molecular weight substances that can be coupled to haptens to form immunogens. Suitable macromolecular carriers include but are not limited to proteins, glycoproteins, polymers, polysaccharides, polypeptides, and nucleic acids that are recognized as foreign and thereby elicit an immunologic response from a host.

The term "polypeptide" refers to any compound formed by the linkage of two or more amino acids via an amide bond. Representative polypeptides include polymers of α-amino acids in which the α-amino group of each non-terminal amino acid residue is linked to the α-carboxyl group of an adjacent residue in a linear chain. High molecular weight polypeptides are referred to as "proteins."

The term "label" refers to an identifying tag that can be attached to a carrier substance or molecule to detect an analyte. A label may be attached to its carrier substance directly or indirectly by means of a linking or bridging moiety. Suitable labels include but are not limited to enzymes (e.g., β-galactosidase, peroxidase, etc.), fluorescent compounds (e.g., rhodamine, fluorescein isothiocyanate or FITC, etc.), luminescent compounds (e.g., dioxetanes, luciferin, etc.), radioactive isotopes (e.g., $^{125}$I), protein-binding partners (e.g., biotin), and the like.

The term "antibody" (abbreviated "Ab") refers to a specific protein capable of binding an immunogen or portion thereof. An antibody is produced in response to an immunogen, which may have been introduced into a host (e.g., an animal or a human) by injection. The generic term "antibody" subsumes polyclonal antibodies, monoclonal antibodies and antibody fragments.

The term "analyte" refers to any substance, or group of substances, the presence or amount of which is to be determined. As used herein, the term "analyte" subsumes the term "antigen," which refers to any compound that can bind to an antibody. Furthermore, as used herein, the term "analyte" refers to all manner of chemical substances including but not limited to: conjugates; immunogens; drugs; drug derivatives; hormones; proteins; antigens; oligonucleotides; and the like. Representative ecstasy drug analytes include but are not limited to MDA, MDMA, MDEA, MDPA, BDB, MBDB, and the like.

The term "derivative" refers to a chemical compound made from a parent compound by one or more chemical reactions.

The term "ligand" refers to any substance or group of substances, such as may be employed in a competitive immunoassay, which behaves similarly to an analyte with respect to binding affinity to an antibody. Representative ligands include but are not limited to drugs, drug derivatives, isomers thereof, hormones, polypeptides, nucleotides, and the like.

The phrase "detecting an analyte" refers to any quantitative, semi-quantitative, or qualitative method, as well as to all other methods for determining an analyte in general, and an ecstasy drug in particular. For example, a method that merely detects the presence or absence of an ecstasy drug in a sample lies within the scope of the present invention, as do methods that provide data as to the amount or concentration of the drug in the sample. The terms "detecting," "determining," "identifying," and the like are used synonymously herein, and all lie within the scope of the present invention.

The phrase "reagent kit" refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for ecstasy drugs. The kit may further comprise ligands of the analyte, and calibration and control materials. The reagents may remain in liquid form or may be lyophilized.

Figure 8:
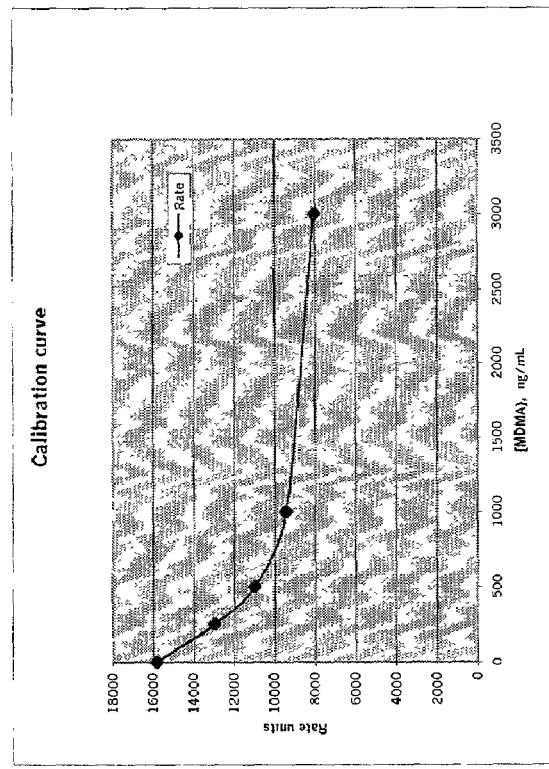
FIG. 8 shows a curve generated using a conjugate and an antibody embodying features of the present invention.

The phrase "calibration and control materials" refers to any standard or reference material containing a known amount of an analyte to be measured. A sample suspected of containing an analyte and the corresponding calibration material are assayed under similar conditions. The concentration of analyte is calculated by comparing the results obtained for the unknown specimen with the results obtained for the standard. This is commonly done by constructing a calibration curve such as is shown in FIG. 8.

The phrase "alkyl group" refers to any straight, branched, cyclic, acyclic, saturated or unsaturated carbon chain. Representative alkyl groups include but are not limited to alkanes, alkenes, alkynes, cycloalkanes, cycloalkenes, cycloalkynes, aryls, and the like, and combinations thereof.

The phrase "optionally substituted" refers to the optional attachment of one or more substituents onto an alkyl group.

The phrase "leaving group" refers to any chemical moiety of a substrate that can be displaced by a reagent reacted therewith. Suitable leaving groups include but are not limited to halides, mesylates, tosylates, alkoxys, quaternary ammonium salts, and the like. Preferred leaving groups for use in accordance with the presently preferred embodiments are provided by activated esters (e.g., trifluoroethoxy esters, N-hydroxysuccinimide esters, p-nitrophenyl esters, pentafluorophenyl esters, imidazolyl esters, N-hydroxybenzotriazolyl esters), whereby the oxygen-containing portion of the ester that is attached to the carbonyl carbon is displaced in the course of the reaction.

The phrase "protecting group" refers to any moiety that is attached to a reactive atom or center in order to alter its usual reactivity. Suitable protecting groups include but are not limited to those described in the treatise entitled *Protective Groups in Organic Synthesis*, 3$^{rd}$ Edition by Theodora W. Greene and Peter G. M. Wuts (John Wiley & Sons, Inc., New York, 1999), the entire contents of which are incorporated herein by reference, except that in the event of any inconsistent disclosure or definition from the present application, the disclosure or definition herein shall be deemed to prevail. Various protecting groups for the nitrogen of amines are known in the art (e.g., vide supra), from amongst which trifluoroacetyl is a presently preferred nitrogen protecting group.

A compound embodying features of the present invention is useful as an intermediate, hapten, or immunogen in the production of antibodies specific for ecstasy drugs. A first series of compounds embodying features of the present invention has a structure I:

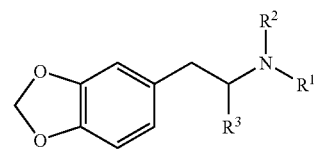

wherein $R^1$ is —J—M—T; $R^2$ is selected from the group consisting of hydrogen, an alkyl group, and a protecting group; and $R^3$ is an optionally substituted alkyl group. J comprises 1–15 carbon atoms and 0–6 heteroatoms. M is selected from the group consisting of —O—, —CO—, —NR$^4$—, —S—, —C(=NH)O—, —NH(CO)—, —NH(CO)NH—, —NH(CS)—, —NH(CS)NH—, —O(CO)NH—, —NH(C=NH)—, and maleimidothioether, wherein $R^4$ is selected from the group consisting of hydrogen and an alkyl group. T is selected from the group consisting of hydrogen, a hydroxyl, a leaving group, a macromolecular carrier, and a label. $R^1$ is not —CH$_2$CN, —CH$_2$C=CH$_2$, —CHO, —CH$_2$CH$_2$OH, —CH$_2$CH$_2$OCH$_3$, or —CH$_2$CCH when $R^2$ is hydrogen and when $R^3$ is methyl.

Preferably, the macromolecular carrier is selected from the group consisting of proteins, polypeptides, and polysaccharides. Preferred proteins include KLH (keyhole limpet hemocyanin), BSA (bovine serum albumin), and BTG (bovine thyroglobulin). Preferably, the alkyl groups comprise straight or branched chains and 1–15 carbon atoms, more preferably 1–11 carbon atoms, and still more preferably 1–9 carbon atoms.

In this first series of preferred embodiments, it is preferred that J comprises —(CH$_2$)$_k$—, wherein k is 1, 2, 3, 4, 5, or 6, and more preferably k is 3. It is further preferred that M is —CO—. Preferably, $R^2$ is hydrogen, methyl, ethyl, n-propyl, or n-butyl, and more preferably $R^2$ is hydrogen. Preferably, $R^3$ is hydrogen, methyl, ethyl, n-propyl, or n-butyl, and more preferably $R^3$ is methyl. Preferably, T is selected from the group consisting of N-oxysuccinimide, a hemocyanin, a globulin, and an albumin, and more preferably, T is selected from the group of proteins consisting of KLH, BSA, and BTG.

FIG. 1 shows a representative scheme for synthesizing compounds and immunogens in accordance with this first series of preferred embodiments. It is to be understood that in this representative synthetic scheme, the starting materials, reagents, individual synthetic transformations, and reaction conditions are purely illustrative, and are not to be construed as limiting. Alternative synthetic preparations, including syntheses based on entirely different starting materials than the ones shown, can be developed without departing from the spirit and scope of the appended claims.

As shown in FIG. 1, the synthesis begins with the ecstasy drug methylenedioxyamphetamine (MDA) 2. The primary amino group of 2 is reacted with 4-bromo-butyric acid ethyl ester to give alkylation product 4. The resultant secondary amino group of 4 is protected using a suitable amino protecting group. As shown in FIG. 1, the amino group of 4 is trifluoroacetylated with trifluoroacetic anhydride (TFAA) to give protected trifluoroacetylated derivative 6. Hydrolysis of the ethyl ester moiety of 6 gives the carboxylic acid derivative 8, which is esterified by reaction with N-hydroxysuccinimide (NHS) to give activated ester derivative 10. Activated ester derivative 10 is reacted with a macromolecular carrier moiety [T] (e.g., KLH, BTG, BSA), deprotected (e.g., with potassium carbonate or at pH13), and dialyzed to provide immunogen 12.

Although the preferred moieties —(CH$_2$)$_3$— and —CO— correspond to J and M, respectively, in compounds 6, 8, 10, and 12 of FIG. 1, it should be emphasized that the specific compounds shown in this synthesis are purely illustrative, and that the synthetic strategy outlined in FIG. 1 can be modified to prepare compounds having substantially different chemical structures. For example, the alkylating agent 4-bromo-butyric acid ethyl ester shown in FIG. 1 can be replaced with a reagent having more or less contiguous methylene units separating the leaving group (e.g., bromide) from the terminal functional group (e.g., the ethyl ester). Similarly, the carbon chain separating these termini can contain heteroatoms, substitution, unsaturation, or the like. Moreover, the functional group introduced through this alkylation step (i.e., the ethyl ester moiety of 4-bromo-butyric acid ethyl ester) can be replaced by a wide array of alternative moieties including but not limited to alcohols, protected alcohols, carboxylic acids, protected carboxylic acids, amines (e.g., primary, secondary, or tertiary), protected amines, thiols, protected thiols, thioethers, amides, thioamides, imides, thioimides, nitriles, imines, hydrazones, maleimidothioethers, and the like, or by any functional group precursor to these moieties that can be converted thereto by one or more synthetic transformations, as is well established in the art.

Although the synthetic strategy outlined in FIG. 1 introduces the —J—M—T moiety through the alkylation of the amino group contained in MDA 2, it should be emphasized that this strategy of elaborating a methylenedioxy-phenyl ring system that already contains nitrogen is purely illustrative, and that numerous alternative strategies can be employed instead. For example, a methylenedioxy-phenyl ring system containing a leaving group in place of the amino group of MDA 2 can be reacted with an amino-containing nucleophile, or with a nucleophile containing a precursor to an amino group (e.g., azide, cyanide, etc.). Indeed, reacting an analogue of MDA 2 containing a leaving group in place of the amino group with an amino analogue of 4-bromo-butyric acid ethyl ester—that is, with NH$_2$—(CH$_2$)$_3$—CO$_2$Et—would also provide compound 6 via a different route. All manner of chemical transformations known in the art—including but not limited to those described in treatises such as *Comprehensive Organic Transformations, 2$^{nd}$ Edition* by Richard C. Larock (Wiley-VCH, New York, 1999) and *March's Advanced Organic Chemistry, 5$^{th}$ Edition* by Michael B. Smith and Jerry March (John Wiley & Sons, Inc., 2001), and references cited therein, are contemplated for use in accordance with the presently preferred embodiments.

Transformations that may prove useful for modifications of the representative synthesis shown in FIG. 1 include but are by no means limited to Fischer esterifications, preparation of other activated esters (e.g., with carbonyldiimidazole, dicyclohexylcarbodiimide, 2-chloropyridinium, 3-chloroisoxazolium, 2,2'-dipyridyl disulfide, 2-pyridyl thiochloroformate, and the like), oxidations (e.g., of alcohols, amines, thiols, thioethers, Baeyer-Villiger oxidation, etc.), reductions (e.g., reduction of nitro group, reductions of carbonyl groups, hydrogenation, etc.), protection of the amino group (e.g., carbamates amides, N-alkyl amines, N-aryl amines, imines, enamines, N-hetero atom derivatives, and the like) and the corresponding deprotections, condensation reactions (e.g., aldol, Claisen, Knoevenagel, etc.), 1,4-addition reactions (e.g., Michael reaction, Corey-Whitesides-House organocuprate coupling, etc.), 1,2-addition reactions (e.g., Grignard reactions, carbonyl reductions, etc.), reduction of nitrites, deprotection of alcohols, deprotection of carboxylic acids, deprotection of ketones, deprotection of aldehydes, reduction of azides, reductions of imines, and the like.

A second series of compounds embodying features of the present invention has a structure II:

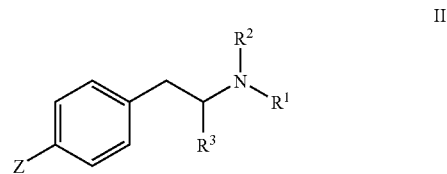

II wherein: $R^1$ is an alkyl group comprising 2–6 carbon atoms; $R^2$ is selected from the group consisting of hydrogen, an alkyl group, and a protecting group; $R^3$ is an optionally substituted alkyl group; and Z is —L—X—Q. L comprises 1–15 carbon atoms and 0–6 heteroatoms. X is selected from the group consisting of —O—, —CO—, —NR$^4$—, —S—, —C(=NH)O—, —NH(CO)—, —NH(CO)NH—, —NH(CS)—, —NH(CS)NH—, —O(CO)NH—, —NH(C=NH)—, and maleimidothioether, wherein $R^4$ is selected from the group consisting of hydrogen and an alkyl group. Q is selected from the group consisting of hydrogen, a hydroxyl, a leaving group, a macromolecular carrier, and a label.

Preferably, the macromolecular carrier is selected from the group consisting of proteins, polypeptides, and polysaccharides. Preferred proteins include KLH (keyhole limpet hemocyanin), BSA (bovine serum albumin), and BTG (bovine thyroglobulin). Preferably, the alkyl groups comprise straight or branched chains and 1–15 carbon atoms, more preferably 1–11 carbon atoms, and still more preferably 1–9 carbon atoms.

In this second series of preferred embodiments, the connectivity of carbon atoms and optional heteroatoms comprising L is unrestricted, and may include straight, branched, cyclic, and acyclic systems. It is preferred that L comprises —(CH$_2$)$_j$—, wherein j is 1, 2, 3, 4, 5, or 6, and more preferably j is 3. It is further preferred that X is —CO—. Preferably, $R^1$ is ethyl, n-propyl, or n-butyl, and more preferably, $R^1$ is ethyl. Preferably, $R^2$ is hydrogen or a protecting group, and more preferably, $R^2$ is a protecting group such as the trifluoroacetyl group. Preferably, $R^3$ is hydrogen, methyl, ethyl, n-propyl, or n-butyl, and more preferably $R^3$ is methyl. Preferably, Q is selected from the group consisting of hydroxy, N-oxysuccinimide, a hemocyanin, a globulin, and an albumin, and more preferably, Q is selected from the group of proteins consisting of KLH, BSA, and BTG.

Figure 2:
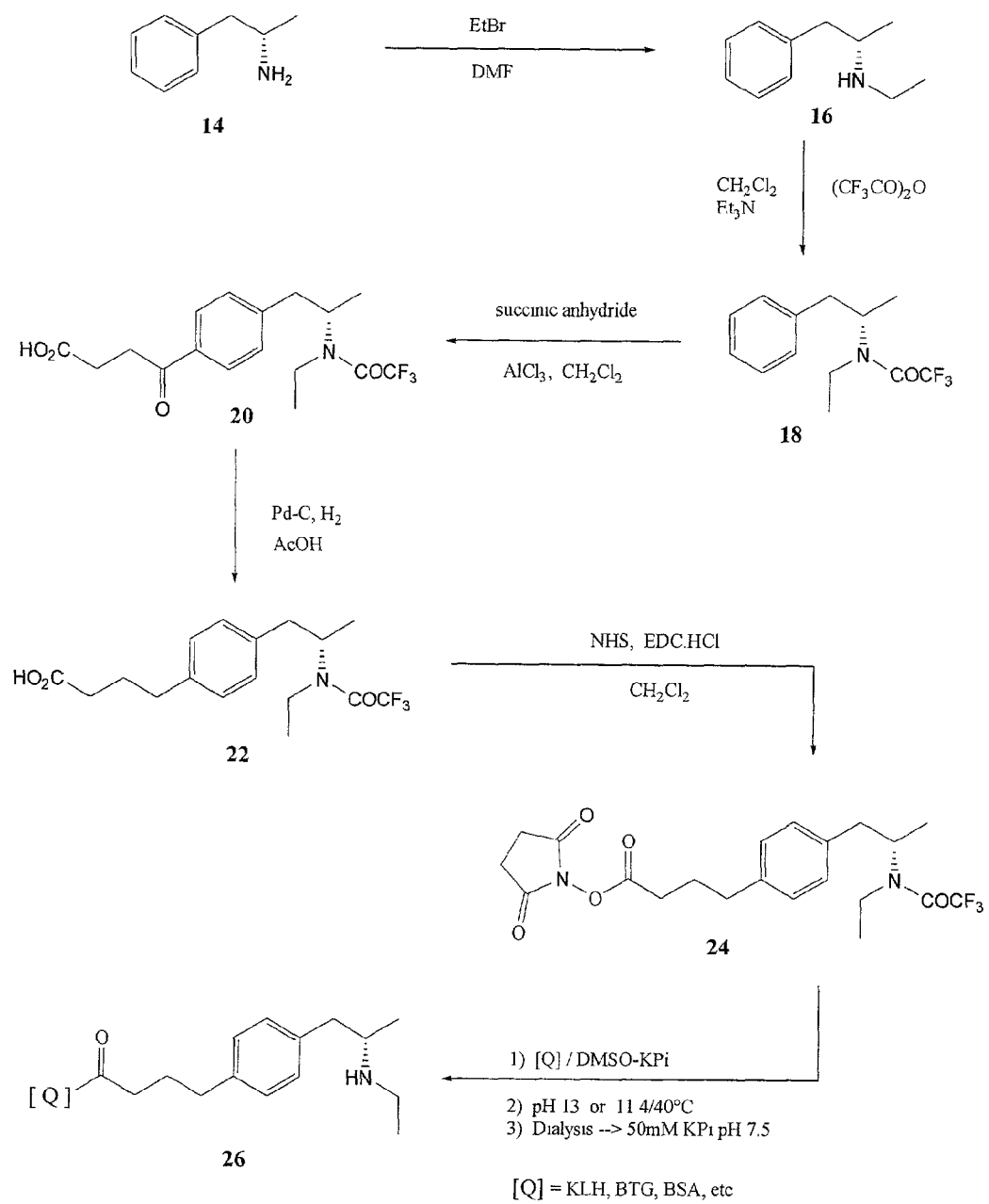
FIG. 2 shows a second representative scheme for synthesizing compounds and immunogens embodying features of the present invention.

FIG. 2 shows a representative scheme for synthesizing compounds and immunogens in accordance with this second series of preferred embodiments. It is to be understood that in this representative synthetic scheme, the starting materials, reagents, individual synthetic transformations, and reaction conditions are purely illustrative, and are not to be construed as limiting. Alternative synthetic preparations, including syntheses based on entirely different starting materials than the ones shown, can be developed without departing from the spirit and scope of the appended claims.

Figure 3:
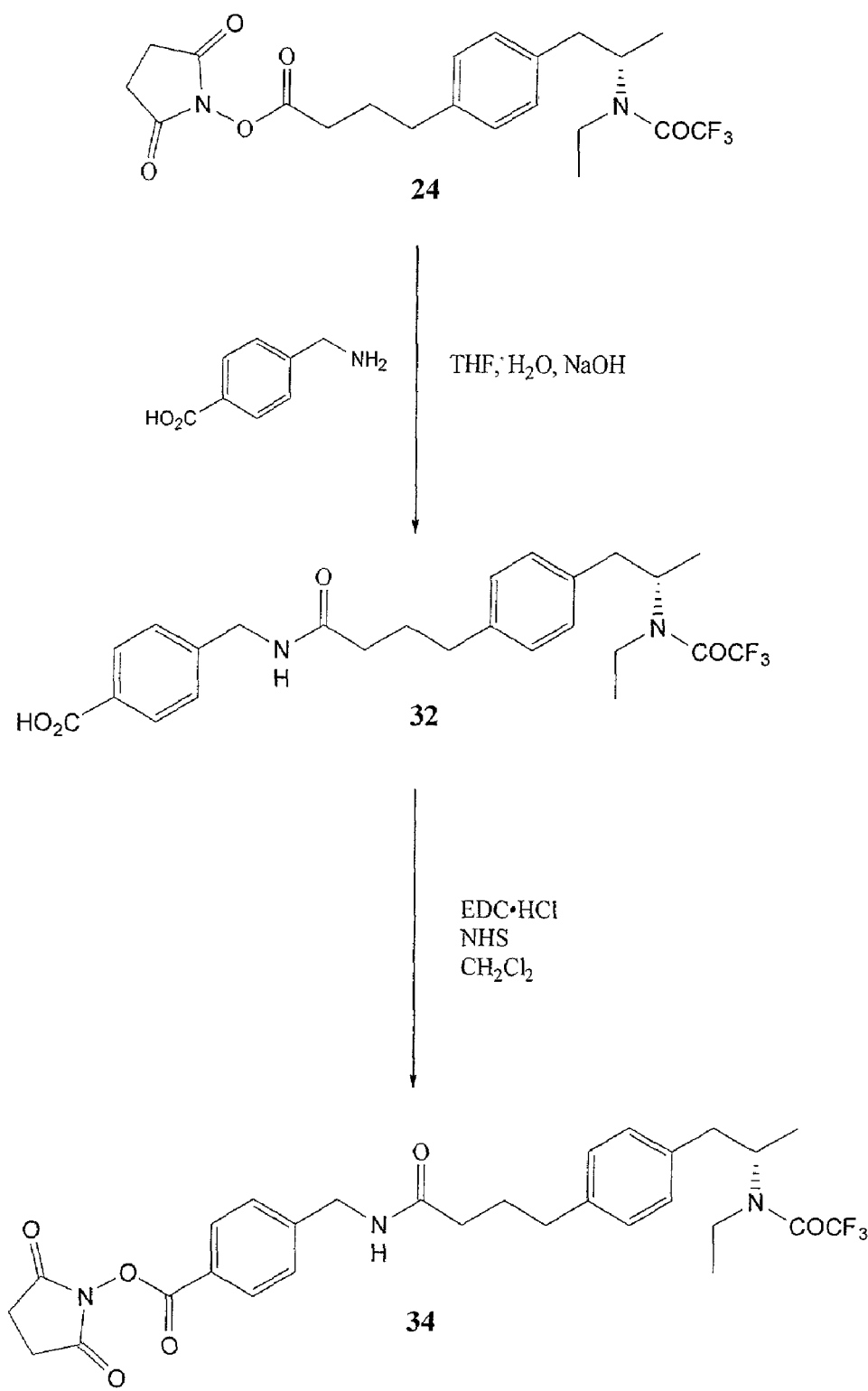
FIG. 3 shows a third representative scheme for synthesizing compounds embodying features of the present invention.

As shown in FIG. 2, the synthesis begins with 1-methyl-2-phenylethylamine-ethylamine 14. The amino group of 14 is alkylated with ethyl bromide to give N-ethylamine derivative 16. The amino group of 16 is protected using a suitable amino protecting group. As shown in FIG. 2, the amino group of 16 is trifluroacetylated with trifluroacetic anhydride (TFAA). Trifluoroacetylated derivative 18 is reacted with succinic anhydride in a Friedel-Crafts type reaction to give carboxylic acid derivative 20. Reduction of the benzyl carbonyl group of carboxylic acid derivative 20 gives reduction product 22, which is esterified by reaction with N-hydroxysuccinimide (NHS) to give the activated ester derivative 24. Activated ester derivative 24 is reacted with a macromolecular carrier moiety [Q] (e.g., KLH, BSA, BTG), the nitrogen deprotected under basic conditions and dialyzed to provide immunogen 26. Alternatively, as shown in FIG. 3, activated ester derivative 24 can be further elaborated, for example, by reaction with 4-aminomethylbenzoic acid to give benzoic acid derivative 32. Benzoic acid derivative 32, and activated ester derivative 34 obtained from 32 by reaction with N-hydroxysuccinimide, are useful intermediates in the synthesis of a wide array of conjugates, labels, and the like in accordance with the present invention. The elaboration strategy outlined in FIG. 3 (i.e., introduction of the aminobenzoate moiety) can be easily adapted for use with methylenedioxy compounds of the type shown in FIG. 1 (e.g., by reacting activated ester derivative 10 with 4-aminomethyl-benzoic acid).

Although the preferred moieties —$(CH_2)_3$— and —CO— correspond to L and X, respectively, in compounds 22, 24, and 26 of FIG. 2, it should be emphasized that the specific compounds shown in this synthesis are purely illustrative, and that the synthetic strategy outlined in FIG. 2 can be modified to prepare compounds having substantially different chemical structures. For example, the succinic anhydride shown in FIG. 2 can be replaced with a cyclic anhydride having more or fewer ring carbon atoms and/or ring heteroatoms, which themselves can be substituted, contain unsaturation, or the like. Moreover, there is no necessity to employ a cyclic anhydride as the Friedel-Crafts acylating agent. Acyclic reagents (e.g., acyl halides, carboxylic acids, ketenes, etc.) can also be employed. Furthermore, there is no necessity to employ a Friedel-Crafts acylation reaction to elaborate the structure of the phenyl ring as shown in FIG. 2. A multitude of alternative electrophilic aromatic substitutions can also be employed including but not limited to Friedel-Crafts alkylation, halogenation, nitration, sulfonation, ipso substitution, and the like. Similarly, the functional group introduced through the Friedel-Crafts acylation step (i.e., the terminal carboxylic acid moiety shown in compounds 20 and 22) can be replaced by or converted to a wide array of alternative moieties including but not limited to alcohols, protected alcohols, protected carboxylic acids, amines (e.g., primary, secondary, or tertiary), protected amines, thiols, protected thiols, thioethers, amides, thioamides, imides, thioimides, nitriles, imines, hydrazones, maleimidothioethers, and the like, or by any functional group precursor to these moieties that can be converted thereto by one or more synthetic transformations, as is well established in the art.

Although the synthetic strategy outlined in FIG. 2 introduces the —L—X—Q moiety through the acylation of the phenyl ring of trifluoroacetylated derivative 18, it should be emphasized that this strategy of elaborating a pre-existing phenyl ring by an electrophilic substitution is purely illustrative, and that numerous alternative strategies could have been employed instead. For example, a phenyl ring substituted with a halogen (e.g., Cl, Br, I) at the position para to the amino-containing side chain can be converted to an organometallic reagent (e.g., a Grignard, an organolithium, an organostannane, an organoborane, an organocuprate, or the like) and reacted with an electrophilic reagent (e.g., a ketone, an aldehyde, an acid halide, a haloalkane, etc.) to form a carbon-carbon bond, using procedures well-known in the art. Alternatively, a phenyl ring substituted with an appropriate leaving group (e.g., Cl, Br, I, alkoxy, etc.) at the position para to the amino-containing side chain can be subjected to a nucleophilic aromatic substitution reaction, using procedures well-known in the art. Furthermore, the substitution pattern of the phenyl ring could be developed on an entirely saturated or partially unsaturated cyclohexane ring system (or precursor thereto), which is aromatized using reagents well-known in the art, including but not limited to hydrogenation catalyts (e.g., Pt, Pd, Ni, etc.), S and Se, quinines, and the like.

As noted above in reference to the synthetic scheme shown in FIG. 1, all manner of chemical transformations known in the art are contemplated for use in accordance with the presently preferred embodiments. Transformations that may prove useful for modifications of the representative synthesis shown in FIG. 2 include but are by no means limited to the ones identified above in reference to the synthetic scheme of FIG. 1, as well as Wolff-Kishner reduction, Clemmensen reduction, the reduction of hydrazones (e.g., using $LiAlH_4$, $NaBH_4$, $NaBH_3CN$, or the like), and the like.

A first antibody embodying features of the present invention is specific for an ecstasy drug. Preferably, the ecstasy drug is selected from the group consisting of MDA, MDMA, MDEA, MDPA, BDB, MBDB, and combinations thereof.

A second antibody embodying features of the present invention is specific for MDEA.

A third antibody embodying features of the present invention is specific for an analyte (i.e., an immunogen, conjugate, or other chemical substance) comprising a structure I or II shown and described above.

Immunogens from the above-mentioned first series of preferred embodiments—that is, the series of compounds comprising a fused methylenedioxy-phenyl ring system (e.g., FIG. 1)—are useful for producing antibodies specific for ecstasy drugs including but not limited to MDA, MDMA, MDEA, MDPA, BDB, MBDB, and combinations thereof. Table 1, shown in FIG. 4, shows cross-reactivity data for several antibodies specific for ecstasy drugs, especially from Fusion #3, and in particular for Ab 2.1.1, which is an antibody generated in response to immunogen 12 of FIG. 1 wherein T is KLH. A classical immunization protocol of the type well established in the art was employed in developing this data. In Table 1, the abbreviation dAM represents d-amphetamine, the abbreviation dMA represents d-methamphetamine, the abbreviation IAM represents I-amphetamine, the abbreviation IMA represents I-methamphetamine, the abbreviation Ses represents sesamin, the abbreviation Phen represents phentermine, the abbreviation Tyr represents tyramine, the abbreviation Pseu represents pseudoephedrine, the abbreviation Eph represents ephedrine, the abbreviation PPA represents phenylpropanolamine, the abbreviation nEpn represents norephedrine, the abbreviation Adr represents adrenaline, arid the abbreviation Ran represents ranitidine (sold under the tradename ZANTAC by Glaxo Wellcome, and distributed by Warner-Lambert Consumer Healthcare, Morris Plains, N.J.).

Figure 5:
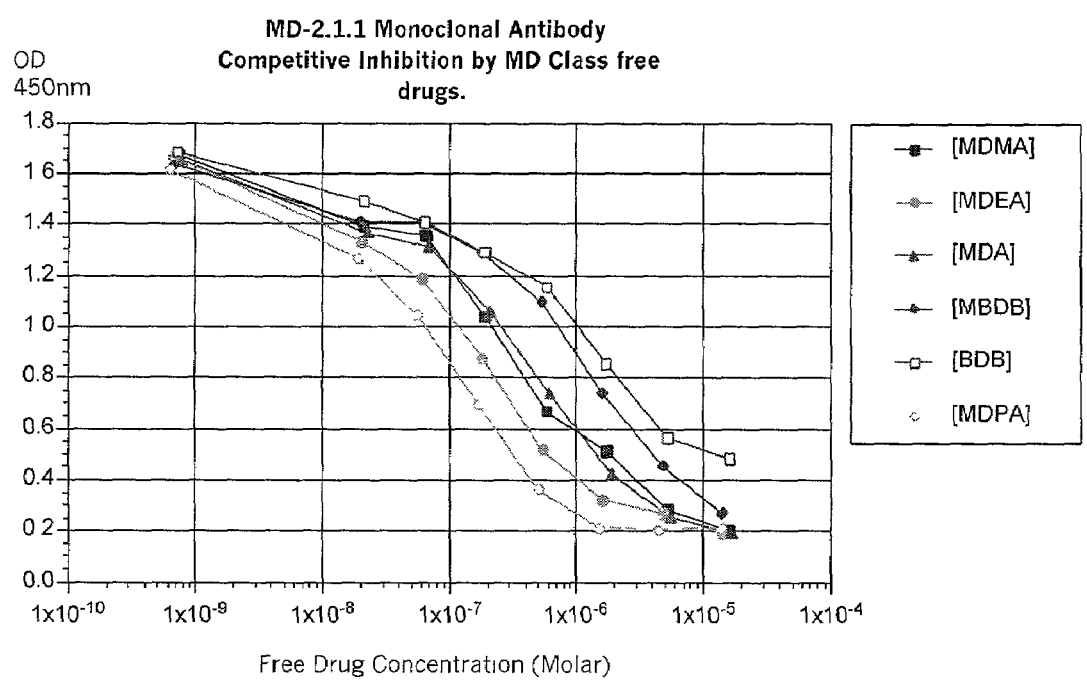
FIG. 5 shows an ELISA plot of competitive inhibition of an antibody embodying features of the present invention by members of the MD class of drugs.
Figure 6:
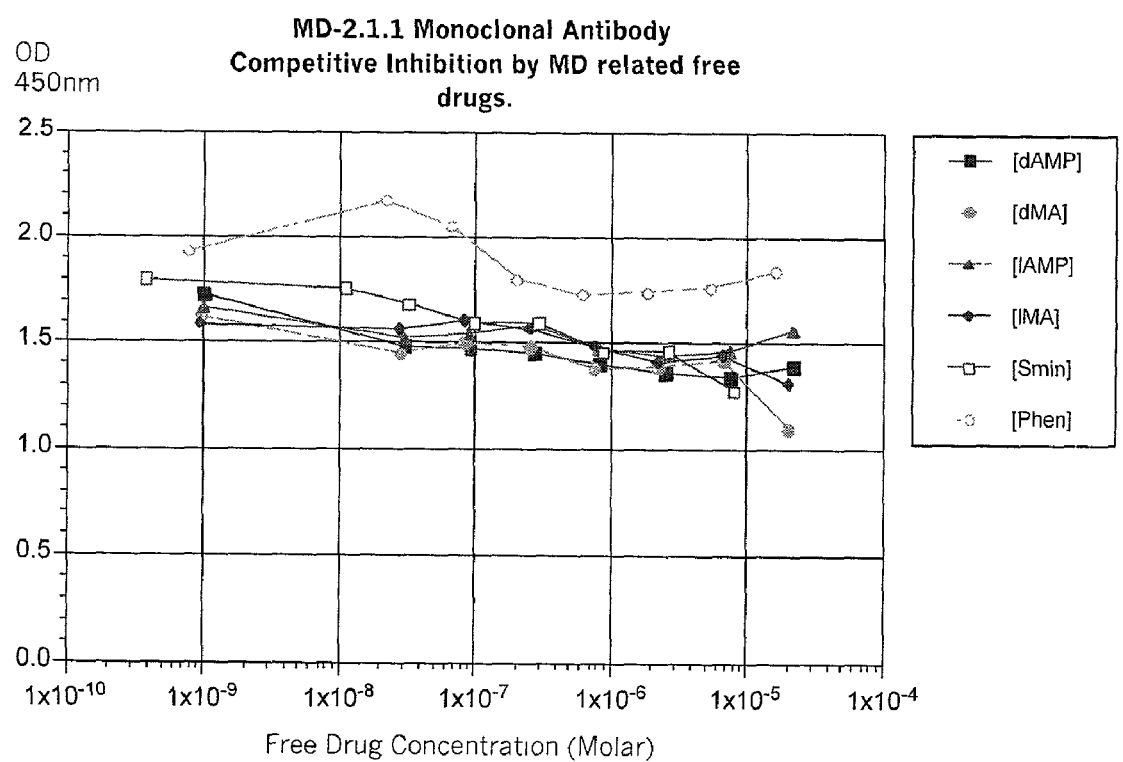
FIG. 6 shows an ELISA plot of competitive inhibition of an antibody embodying features of the present invention by related drug derivatives.

Antibodies elicited by the immunogen 12 (e.g., wherein T is KLH) show good response and specificity to ecstasy drugs, as shown by the competitive inhibition plot in FIG. 5. Furthermore, these antibodies show little or no cross-reactivity to related drugs, as shown by the competitive inhibition plot in FIG. 6. In FIG. 6, the abbreviation dAMP represents d-amphetamine, the abbreviation IAMP represents I-amphetamine, and the abbreviation Smin represents sesamin, while the abbreviation IMA, dMA, and Phen have the same meanings as in Table 1 described above.

Table 2 shows cross-reactivity data for the antibody MDMA-2.1.1 that is generated in response to immunogen 12 of FIG. 1 wherein T is KLH. By determining the drug concentration that results in a 50% reduction in binding (ED 50) of a standard, methamphetamine, dividing by the ED50 of each other drug, and then multiplying the result by 100, the percent cross-reactivities shown in Table 2 can be calculated. The antibodies used in developing this data were produced through a classical immunization protocol of the type well established in the art.

TABLE 2

Cross-reactivity of MDMA-2.1.1 for various drugs.

| Drug | % Cross-reactivity |
|---|---|
| d-MDMA | 100 |
| MDEA | 204 |
| MDA | 60.6 |
| MBDB | 26.1 |
| BDB | 20.5 |
| MDPA | 365 |
| d-AMP | 0 |
| d-MAMP | 0.65 |
| I-AMP | 0 |
| I-MAMP | 0 |
| Sesamin | 0 |
| Phentermine | 0 |
| Tyramine | 0 |
| Pseudoephedrine | 0 |
| Ephedrine | 0 |
| Phenylpropanolamine | 0 |
| Norepinephrine | 0 |
| Adrenaline | 0 |
| Ranitidine (ZANTAC) | 0 |

Immunogens from the above-mentioned second series of preferred embodiments—that is, the series of compounds lacking a fused methylenedioxy-phenyl ring system—are useful for producing antibodies specific for ecstasy drugs including but not limited to MDA, MDMA, MDEA, MDPA, BDB, MBDB, and combinations thereof. Antibodies produced in response to N-ethyl substituted immunogens from this second series (i.e., $R^1$ in structure II is ethyl) show particularly high recognition for the ecstasy drug MDEA ("Eve"), which is generally poorly detected by conventional amphetamine and methamphetamine immunoassays. An antibody thus produced can be used either as a booster antibody to increase detection in an existing amphetamine or methamphetamine assay or as a separate antibody for MDEA in immunoassays for MD-class drugs.

Table 3 shows cross-reactivity data for the antibody NEAMP-1.3, which is generated in response to immunogen 26 of FIG. 2 wherein Q is KLH. By the procedure described above, the percent cross-reactivities shown in Table 3 can be calculated. The antibodies used in developing this data can be produced using a classical immunization protocol.

TABLE 3

Cross-reactivity of NEAMP-1.3 for various drugs

| Drug | Percent Cross-Reactivity |
|---|---|
| d-methamphetamine | 100 |
| I-methamphetamine | nd |
| d-amphetamine | 32.5 |
| I-amphetamine | 33.5 |
| MDMA | 114 |
| MDEA | 507 |
| MDBD | 20 |
| Phendimetrazine | 0.6 |
| Pseudoephedrine | 2.0 |
| I-ephedrine | 6.7 |
| Ranitidine (ZANTAC) | 0.2 |

Figure 7:
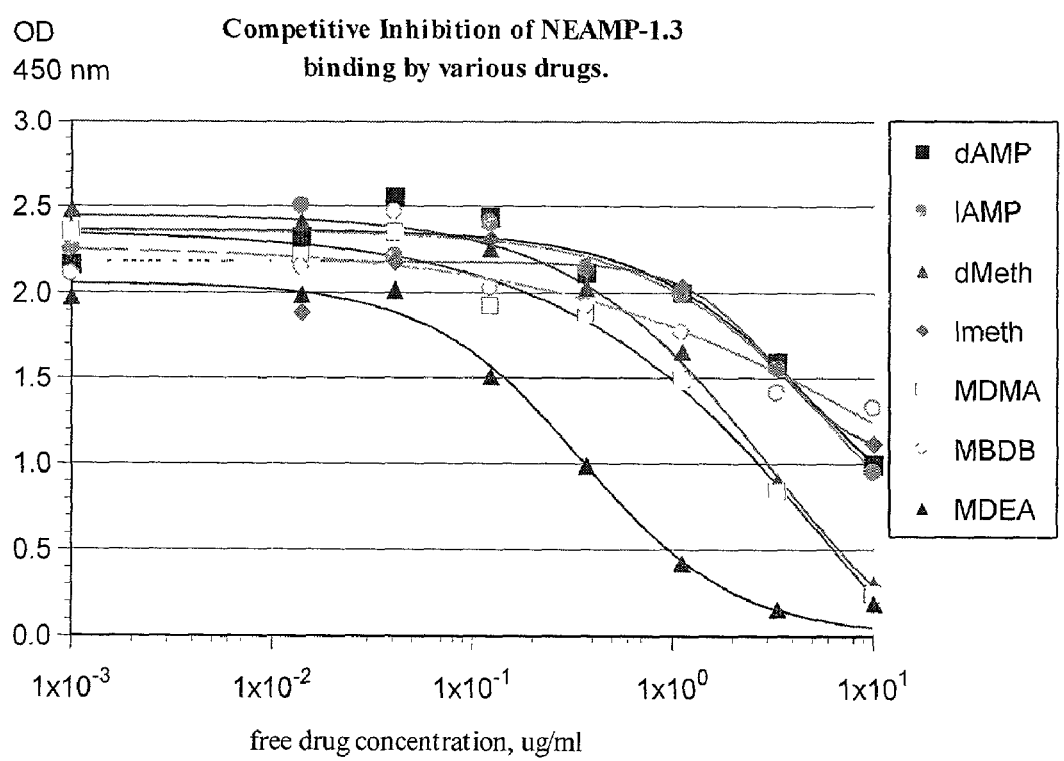
FIG. 7 shows an ELISA plot of competitive inhibition of an antibody embodying features of the present invention by various drugs

Antibodies elicited by the N-ethyl substituted immunogen 26 (e.g., wherein Q is KLH) show good response and specificity to ecstasy drugs in general, and to MDEA in particular, as shown by the competitive inhibition plot in FIG. 7. In FIG. 7, the abbreviation dMeth represents d-methamphetamine, and the abbreviation lmeth represents l-methamphetamine.

A reagent kit embodying features of the present invention comprises an antibody embodying features of the present invention. A representative reagent kit may comprise an antibody specific for an ecstasy drug, a complex comprising a ligand of an ecstasy drug or a derivative thereof coupled to a labeling moiety, and may optionally also comprise one or more calibrators comprising a known amount of an ecstasy drug or a related standard.

Antibodies embodying features of the present invention can be included in a kit, container, pack, or dispenser together with instructions for their utilization. When the antibodies are supplied in a kit, the different components of the immunoassay may be packaged in separate containers and admixed prior to use. Such packaging of the components separately may permit long-term storage without substantially diminishing the functioning of the active components. Furthermore, reagents can be packaged under inert environments (e.g., under a positive pressure of nitrogen gas, argon gas, or the like), which is especially preferred for reagents that are sensitive to air and/or moisture.

Reagents included in kits embodying features of the present invention can be supplied in all manner of containers such that the activities of the different components are substantially preserved, while the components themselves are not substantially adsorbed or altered by the materials of the container. Suitable containers include but are not limited to ampules, bottles, test tubes, vials, flasks, syringes, envelopes (e.g., foil-lined), and the like. The containers may be comprised of any suitable material including but not limited to glass, organic polymers (e.g., polycarbonate, polystyrene, polyethylene, etc.), ceramic, metal (e.g., aluminum), metal alloys (e.g., steel), cork, and the like. In addition, the containers may comprise one or more sterile access ports (e.g., for access via a needle), such as may be provided by a septum. Preferred materials for septa include rubber and polytetrafluoroethylene of the type sold under the trade name TEFLON by DuPont (Wilmington, Del.). In addition, the containers may comprise two or more compartments separated by partitions or membranes that can be removed to allow mixing of the components.

Reagent kits embodying features of the present invention may also be supplied with instructional materials. Instructions may be printed (e.g., on paper) and/or supplied in an electronic-readable medium (e.g., floppy disc, CD-ROM, DVD-ROM, zip disc, videotape, audio tape, etc.). Alternatively, instructions may be provided by directing a user to an Internet web site (e.g., specified by the manufacturer or distributor of the kit) and/or via electronic mail.

As noted above, reagent kits embodying features of the present invention may comprise calibration or control materials, which comprise a known amount of the analyte to be measured. The concentration of an analyte can be calculated by comparing results obtained for the sample with results obtained for the standard. A calibration curve can be constructed and used for relating the sets of results, and for determining the concentration of an analyte in a sample. FIG. 8 shows a curve on a HITACHI Analyzer using modified Roche ONLINE formats and reagents and Ab MDMA 2.1.1 (i.e., the antibody elicited from immunogen 12 in which T is KLH).

Methods of detecting an analyte that embody features of the present invention comprise contacting a sample with an antibody embodying features of the present invention, binding the antibody to the analyte, and detecting an adduct formed by the antibody and the analyte.

Any sample that is suspected of containing an analyte (e.g., an ecstasy drug) can be analyzed in accordance with the methods of the presently preferred embodiments. The sample can be pretreated if desired and can be prepared in any convenient medium that does not interfere with the assay. Preferably, the sample comprises an aqueous medium, such as a body fluid from a host. Representative bodily fluids include but are not limited to urine, whole blood, plasma, serum, saliva, semen, stool, sputum, cerebral spinal fluid, tears, mucus, and the like, and combinations thereof. Preferably, the bodily fluid comprises a plasma, serum, or urine.

It is to be understood that all manner of immunoassays employing antibodies are contemplated for use in accordance with the presently preferred embodiments, including assays in which antibodies are bound to solid phases and assays in which antibodies are in liquid media. Methods of immunoassay that can be used to detect analytes using antibodies embodying features of the present invention include but are not limited to: competitive (reagent limited) assays wherein labeled analyte and analyte in a sample compete for antibodies; single-site immunometric assays wherein the antibody is labeled; two-site immunometric (reagent excess) assays wherein a capture antibody (i.e., an antibody attached to a solid phase) binds a first epitope of an antigen, and wherein a detecting antibody (i.e., a labeled antibody) binds to the antigen-capture antibody complex; and the like.

Procedures for performing various types of immunoassays are well established in the art and are set forth in numerous treatises and publications including *The Immunoassay Handbook*, $2^{nd}$ Edition edited by David Wild (Nature Publishing Group, 2000), the entire contents of which are incorporated herein by reference, except that in the event of any inconsistent disclosure or definition from the present application, the disclosure or definition herein shall be deemed to prevail.

Methods of producing antibodies embodying features of the present invention comprise inoculating a host with an immunogen embodying features of the present invention. Suitable hosts include but are not limited to mice, rats, hamsters, guinea pigs, rabbits, chickens, donkeys, horses, monkeys, chimpanzees, orangutans, gorillas, humans, and any species capable of mounting a mature immune response. The immunization procedures used are well established in the art and are set forth in numerous treatises and publications including *The Immunoassay Handbook*, $2^{nd}$ Edition cited above, and the references cited therein.

Preferably, an immunogen embodying features of the present invention is administered to a host subject (e.g., an animal or a human) in combination with an adjuvant. Suitable adjuvants include but are not limited to Freund's adjuvant, powdered aluminum hydroxide (alum), aluminum hydroxide together with Bordetella pertussis, and monophosphoryl Lipid A synthetic-trehalose dicorynomycolate (MPL-TDM).

Polyclonal antibodies can be raised in a mammalian host by one or more injections of an immunogen, which can optionally be administered together with an adjuvant. Typically, an immunogen (or a combination of an immunogen and an adjuvant) is injected into a mammalian host by one or multiple subcutaneous or intraperitoneal injections. Preferably, the immunization program is carried out over at least one week, and more preferably over two or more weeks. Polyclonal antibodies produced in this manner can be isolated and purified utilizing methods well-known in the art.

Monoclonal antibodies can be produced by the well-established hybridoma methods of Köhler and Milstein (e.g., *Nature*, 1975, 256, pp. 495–497). Hybridoma methods typically involve: (1) immunizing a host or lymphocytes from a host; (2) harvesting the monoclonal antibody secreting (or having the potential to secrete) lymphocytes; (3) fusing the lymphocytes to immortalized cells; and (4) selecting cells that secrete the desired monoclonal antibody.

A host can be immunized to elicit lymphocytes that produce or are capable of producing antibodies specific for an immunogen. Alternatively, the lymphocytes can be immunized in vitro. If human cells are desired, peripheral blood lymphocytes (PBLs) can be used, although spleen cells or lymphocytes from other mammalian sources are preferred.

The lymphocytes can be fused with an immortalized cell line to form hybridoma cells, a process which can be facilitated by the use of a fusing agent (e.g., polyethylene glycol). By way of illustration, mutant rodent, bovine, or human myeloma cells immortalized by transformation can be used. Substantially pure populations of hybridoma cells—as opposed to unfused immortalized cells—are preferred. Thus, following fusion, the cells can be grown in a suitable medium that inhibits the growth or survival of unfused, immortalized cells, for example, by using mutant myeloma cells that lack the enzyme hypoxanthine guanine phosphoribosyl transferase (HGPRT or HPRT). In such an instance, hypoxanthine, aminopterin and thymidine can be added to the medium (HAT medium) to prevent the growth of HGPRT-deficient cells while permitting hybridomas to grow.

Preferably, immortalized cells fuse efficiently, can be isolated from mixed populations by selection in a medium such as HAT, and support stable and high-level expression of antibody following fusion. Preferred immortalized cell lines include myeloma cell lines available from the American Type Culture Collection (Manassas, Va.).

Because hybridoma cells typically secrete antibody extracellularly, the culture media can be assayed for the presence of monoclonal antibodies specific for the MD-class of amphetamine derivatives. Immunoprecipitation or in vitro binding assays—for example, radio immunoassay (RIA) or enzyme-linked immunoabsorbent assay (ELISA)—can be used to measure the binding specificity of monoclonal antibodies.

Monoclonal antibody secreting hybridoma cells can be isolated as single clones by limiting dilution procedures and sub-cultured. Suitable culture media include but are not limited to Dulbecco's Modified Eagle's Medium, RPMI-1640, and polypeptide-free or polypeptide-reduced or serum-free media (e.g., Ultra DOMA PF or HL-1, available from Biowhittaker; Walkersville, Md.). Alternatively, the hybridoma cells can be grown in vivo as ascites.

Monoclonal antibodies can be isolated and/or purified from a culture medium or ascites fluid by conventional Ig purification procedures including but not limited to: polypeptide A-Sepharose, hydroxylapatite chromatography; gel electrophoresis; dialysis; ammonium sulfate precipitation; and affinity chromatography.

Monoclonal antibodies can also be produced by recombinant methods, such as are described in U.S. Pat. No. 4,166,452. DNA encoding monoclonal antibodies can be isolated and sequenced using conventional procedures (e.g., using oligonucleotide probes that specifically bind to murine heavy and light antibody chain genes), preferably to probe DNA isolated from monoclonal antibody hybridoma cell lines secreting antibodies specific for ecstasy drugs. The isolated DNA fragments can be sub-cloned into expression vectors that are then transfected into host cells—for example, simian COS-7 cells, Chinese hamster ovary (CHO) cells, or myeloma cells that do not otherwise produce Ig polypeptide—to express monoclonal antibodies. The isolated DNA fragments can be modified by substituting the coding sequence for human heavy and light chain constant domains in place of the homologous murine sequences, as described in U.S. Pat. No. 4,816,567, or by fusing the Ig coding sequence to all or a portion of the coding sequence for a non-Ig polypeptide. Such a non-Ig polypeptide can be substituted for the constant domains of an antibody, or can be substituted for the variable domains of one antigen-combining site to create a chimeric bivalent antibody.

The following representative procedures for preparing immunogens embodying features of the present invention and for developing hybridomas to ecstasy drugs are provided solely by way of illustration, and are not intended to limit the scope of the appended claims or their equivalents.

EXAMPLES

General

Chemical reagents were obtained from Aldrich Chemical Co., Milwaukee, Wis., USA, unless otherwise stated. Solvents were obtained from either J T Baker or Fisher Scientific and were of ACS or HPLC grade or better, unless otherwise stated. Methylene chloride ($CH_2Cl_2$) was dried by distillation over and from calcium hydride. Tetrahydrofuran (THF) was dried by distillation over and from sodium and benzophenone. Dry dimethylformamide (DMF) was obtained from Aldrich Chemical Co. in sealed SURESEAL bottles. Column chromatography was performed using E.M. Science flash-grade silica gel (Cat. # 9385-9; Silica gel 60; 230–400 mesh ASTM). Thin layer chromatography was performed using silica gel plates obtained from E.M. Science (Cat. # 5715-7; 0.025 cm thickness). "KPi" refers to potassium phosphate buffer. Mixed solvents are expressed as volume for volume percentages (e.g., 10% MeOH—$CHCl_3$ or 10% MeOH in $CHCl_3$ is chloroform containing 10% of methanol by volume).

Representative Synthetic Procedures

Synthesis of MDA Derivative 4 a) A suspension/solution of 700 mg of methylenedioxyamphetamine hydrobromide salt in methylene chloride ($CH_2Cl_2$) was shaken thoroughly with saturated aqueous (sat. aq.) sodium bicarbonate ($NaHCO_3$). The layers were separated and the aqueous layer extracted repeatedly with additional $CH_2Cl_2$ until only negligible organic material was being extracted. The combined organic layers were evaporated to dryness under reduced pressure (rotary evaporator; rotovap) and briefly dried further under high vacuum to give 408 mg of the free base of methylenedioxyamphetamine 2 as an oil.

b) To a solution of 400 mg of the free base 2 in 5 mL of dry dimethylformamide (DMF) was added 387 μL (1.2 mol. equiv.) of ethyl 4-bromobutyrate (Fluka Chemical Co.) and the reaction stirred overnight (O.N.) at room temperature (RT) under argon. The reaction mixture was diluted with 20 mL of $CH_2Cl_2$, stirred with 25 mL of sat. aq. $NaHCO_3$, the layers separated, the aq. layer extracted with 50 mL $CH_2Cl_2$ followed by 50 mL ethyl acetate (EtOAc), the organic extracts combined, dried over sodium sulfate ($Na_2SO_4$), evaporated under reduced pressure (rotovap) and the residue dried under high vacuum (manifold) to give 520 mg of the product 4, shown by $^1$H-NMR to be about 90% pure. The material was used without further purification in the next step.

Material obtained from the extraction of a similar reaction after the aqueous quench indicated the presence of the product 4 as the HBr salt, together with small amounts of the disubstituted product, by $^1$H-NMR. Silica gel chromatographic purification [$1^{st}$ column: 20% methanol (MeOH) in chloroform ($CHCl_3$) as eluent; $2^{nd}$ column: EtOAc—MeOH—acetone—water (6:1:1:1) as eluent] gave clean product 4. Mass spec: M−H, 292.

Synthesis of 6

To a solution of 500 mg of crude 4 and 950 μL (4 mol. equiv.) of triethylamine in dry $CH_2Cl_2$ under argon and cooled to ~0° C. (ice bath) was added 289 μL (1.2 mol. equiv.) of trifluoroacetic anhydride (TFAA). The reaction was allowed to warm up to RT while stirring overnight. The reaction was diluted to a volume of 50 mL with $CH_2Cl_2$, washed with water (2×50 mL), sat. aq. $NaHCO_3$ (2×50 mL), sat. aq. sodium chloride (NaCl) (1×50 mL), dried over $Na_2SO_4$, evaporated (rotovap) and dried under high vacuum to give ~730 mg of crude product. The material was chromatographed on silica gel, eluting with 30% EtOAc in hexanes, to give 449 mg of the product 6 as a pale colored liquid. Mass spec (M+H): Observed, 389.1449; Calc, 389.1450.

Synthesis of 8

A solution of 445 mg of 6 in 2 mL of THF and 2 mL of 3-Normal (3N) perchloric acid was stirred at 50° C. (oil bath) under argon for 4.5 hours. The reaction was poured into 75 mL of water, the mixture extracted with EtOAc (2×50 mL), the organic extracts washed with water, dried ($Na_2SO_4$) and evaporated (rotovap) to give 416 mg of crude product. The material was chromatographed on silica gel, eluting with 5% MeOH in $CH_2Cl_2$, the fractions containing product combined, evaporated (rotovap) and dried under high vacuum to give 320 mg of product 8 as a collapsing foam. Low Resolution Mass spec: (M+H): Observed, 362.1. High Resolution Mass Spec: (M+Na): Observed, 384.1024; Calc, 384.1035.

Synthesis of 10

A solution of 310 mg of 8 in 20 mL of dry $CH_2Cl_2$ under argon was treated with 296 mg (3 mol. equiv.) of N-hydroxysuccinimide followed by 329 mg (2 mol. equiv.) of 1-ethyl-3-(3-dimethylaminopropyl)carbodiimide hydrochloride (EDC.HCl) (Sigma Chemical Co.) and stirred O.N. at RT. The reaction was washed with water (1×20 mL), sat. aq. NaHCO$_3$ (2×20 mL), sat. aq. NaCl (1×20 mL), dried (Na2SO4) and evaporated (rotovap). The residue was chromatographed on silica gel, eluting with 30% EtOAc in hexanes, the product fractions combined and evaporated (rotovap). The residue was redissolved in dry CH$_2$Cl$_2$ and re-evaporated (×6), then dried under high vacuum, to give 280 mg of the NHS ester derivative 10 as a white/colorless collapsing foam. High Res Mass Spec: (M+H): Observed, 459.1381; Calc, 459.1379.

Synthesis of MDMA Immunogen 12 (T=KLH; 12a)

To a stirring solution of 220 mg of purified keyhole limpet hemocyanin (KLH) in 13 mL of 50 mM Kpi pH 7.5 cooled in an ice-water bath was added 4.33 mL of dimethylsulfoxide (DMSO) dropwise, to give a solution of KLH in 25% DMSO—KPi. 1.58 mL, equivalent to ~20 mg protein, was withdrawn for use as the control. To the remainder was added a solution of 26 mg of 10 (~0.6 equiv. per lysine in KLH) dissolved in a total of 1.5 mL DMSO, giving a reaction of 10 with KLH in ~31% DMSO—KPi. The ice bath was removed and the reaction (stoppered flask) stirred overnight. The opalescent gray reaction was transferred to dialysis tubing (15,000 MW cut-off; SpectraPor 7) and dialyzed sequentially against 30% DMSO—KPi/RT (3×1.1 L), 15% DMSO—KPi/RT, then KPi (1×2.2 L/RT ->~4° C.; 5×2.2 L/~4° C.) (all KPi was 50 mM KPi pH 7.5). The control KLH was also transferred to dialysis tubing (15,000 MW cut-off; SpectraPor 7) and dialyzed separately against 30% DMSO—KPi, then placed in the same dialysis vessel with the immunogen when stepping down to 15% DMSO—KPi. 1 mL of the retentate was removed for determination of the extent of lysine modification. The remainder was dialyzed against 50 mM K$_2$CO$_3$ (4×2.2 L/RT/2 days) then against KPi (4×2.2 L/~4° C.). Deprotection of the amine was completed by redialysis against pH 13 buffer (50 mM K$_2$CO$_3$ basified with KOH to pH 13) at RT for ~7 days followed by dialysis back into 50 mM KPi pH 7.5 (3 changes) to give the MDMA immunogen 12 (T=KLH; 12a) as an almost colorless clear solution. Coomassie Blue protein assay (modified Bradford assay) (Biorad Laboratories, Hercules, Calif., USA) gave 1.9 mg/mL protein. Trinitrobenzenesulfonic acid (TNBS) assay on the undeprotected immunogen (vide supra) (after protein concentration determination via the Comassie Blue assay) gave 38% modification of available lysines on KLH.

Synthesis of the MDMA Conjugate 12 (T=BSA; 12b)

To a stirring solution of 0.55 g of bovine serum albumin (BSA) (Pentex Fraction V; Miles Inc., Kankakee, Ill., USA) in 11 mL of 50 mM KPi pH 7.5 cooled in an ice-water bath was added 4.0 mL of DMSO dropwise. From the resulting solution of BSA in ~27% DMSO—KPi was withdrawn 1.36 mL., containing ~0.05 g of BSA, for use as the control if needed. To the remaining solution was added 8.2 mg (~2.4 mol. equiv.) of 10 dissolved in a total of 0.6 mL of DMSO, resulting in a mixture of 10 and BSA in 30% DMSO—KPi. The ice-water bath was removed and the reaction allowed to stir overnight in a stoppered flask. The clear reaction was transferred to dialysis tubing (15,000 MW cut-off; SpectraPor 7) and dialyzed sequentially against 30% DMSO—KPi/RT (1.1 L), 15% DMSO—KPi/RT (1.1 L), KPi/RT (1×1.1), then 50 mM K$_2$CO$_3$ (4×1.1 L/RT/2 days) against KPi (4×2.2 L/~4° C.) (all KPi was 50 mM KPi pH 7.5). The control KLH was also transferred to dialysis tubing (15,000 MW cut-off; SpectraPor 7) and dialyzed separately against 30% DMSO—KPi, then placed in the same dialysis vessel with the immunogen when stepping down to 15% DMSO—KPi and carried forwards alongside. Analysis of a portion of the retentate here showed the protein concentration to be 18.9 mg/mL (Coomassie Blue protein assay) and the substitution by hapten to be ~1.6 (Difference UV, against the BSA control). Deprotection of the amine was completed by redialysis against pH 13 buffer (50 mM K$_2$CO$_3$ basified with KOH to pH 13) at RT for ~4 days followed by dialysis back into 50 mM KPi pH 7.5 (4 changes) to give the MDMA conjugate 12 (T=BSA; 12b) as a colorless clear solution. The protein concentration was determined by UV (OD$_{280}$ of conjugate taken to be approximately the same as OD$_{280}$ of parent BSA=0.6 at 1 mg/mL) to be approximately 1.9 mg/mL protein.

Synthesis of N-ethylamphetamine 16

5.0 g of d-amphetamine sulfate (Sigma Chemical Co., St. Louis, Mo., USA) was treated with 100 mL of CH$_2$Cl$_2$ and 30 mL of 1N NaOH and stirred vigorously for 15 min. The layers were separated and the aqueous portion was extracted with 25 mL of CH$_2$Cl$_2$. The organic portions were combined, dried over anhydrous Na$_2$SO$_4$ and conc. at reduced pressure to give 3.66 g of d-amphetamine free base 14 as a clear oil. This was dissolved in 30 mL of anhydrous DMF and treated with 2.9 g of ethyl bromide and stirred at room temp. for 3 days. The mixture was conc. at reduced pressure to yield 6.6 g and used crude in the next step. The product contains some starting material and diethylated by-product, which is difficult to purify by column chromatography.

Synthesis of 18

A solution of 6.6 g of crude N-ethylamphetamine in 75 mL of anhydrous CH$_2$Cl$_2$ was treated with 10 mL of triethylamine. The mixture was cooled with an ice bath and treated with 4.3 mL of trifluoroacetic anhydride and stirred at room temp. under argon overnight. The mixture was conc. at reduced pressure. The residue was dissolved in 75 mL of EtOAc and washed with 3×25 mL of sat. NaHCO$_3$, 25 mL of H$_2$O, 25 mL of sat. brine, dried over anhydrous Na$_2$SO$_4$ and conc. at reduced pressure. The residue was chromatographed on 300 g of silica gel using 30% EtOAc-hexane as eluent to yield 4.0 g of clear oil which still contained some diethylated by-product from the previous step. This was rechromatographed on 250 g of silica gel using 5% EtOAc-hexane as eluent to yield 2.6 g of 18 as a clear oil.

Synthesis of 20

A solution of 2.0 g of 18 in 50 mL of anhydrous CH$_2$Cl$_2$ under argon was treated with 1.2 g of succinic anhydride. The mixture was cooled with an ice bath then treated with 4.0 g of AlCl$_3$ added portionwise. The reaction was stirred at 0° C. for 2 hrs., then at room temp. overnight. The mixture was treated with 18 mL of 3N HCl added slowly at first, then stirred vigorously for 30 min. The layers were separated and the organic layer was washed with 25 mL of H$_2$O and 25 mL of sat. brine, dried over Na$_2$SO$_4$ and conc. at reduced pressure to an amber oil. This was chromatographed on 150 g of silica gel using 3% MeOH—CH$_2$Cl$_2$ as eluent to yield 2.6 g of 20 as an amber oil.

Synthesis of 22

A 500 mL Parr bottle was charged with 115 mg of 10% Pd/C followed by a solution of 600 mg of 20 in 30 mL of acetic acid and hydrogenated at 50 PSI for 17 hrs. The catalyst was filtered off through the filter agent sold under the tradename CELITE by Celite Corporation (available from Aldrich Chemical Company, Inc., Milwaukee, Wis.) and the filtrate was conc. at reduced pressure. Residual acetic acid was driven off by evaporating 5 times with 25 mL of toluene. The toluene was driven off by evaporating 5 times with $CH_2Cl_2$ to yield 576 mg of 22 as an amber oil.

Synthesis of 24

A solution of 576 mg of 22 in 25 mL of anhydrous $CH_2Cl_2$ under argon was treated with 260 mg of N-hydroxysuccinimide followed by 435 mg of 1-ethyl-3-(3-dimethylaminopropyl)carbodiimide HCl and stirred at room temp. overnight. The mixture was washed with 25 mL of 0.1 N HCl, 25 mL of $H_2O$, 2×25 mL of sat. $NaHCO_3$, 25 mL of sat. brine, dried over $Na_2SO_4$ and conc. at reduced pressure to yield 735 mg of 24 as an amber oil.

Synthesis of 32

A mixture of 108 mg of 4-(aminomethyl)benzoic acid in 5 mL of $H_2O$ and 10 mL of distilled THF was treated with a solution of 315 mg of 24 in 10 mL of distilled THF, followed by 1.2 mL of 1N NaOH and stirred at room temp. for 1 hr. The pH of the reaction is 9. The THF was removed at reduced pressure and the aqueous residue was diluted with 5 mL of $H_2O$, and acidified to pH 6 with 6N HCl. This was extracted with 2×15 mL of EtOAc. The EtOAc extracts were combined, dried over anhydrous $Na_2SO_4$ and conc. in vacuo to yield 290 mg of 32 as a white amorphous solid.

Synthesis of 34

A solution of 270 mg of 32 in 10 mL of anhydrous $CH_2Cl_2$ under argon was treated with 85 mg of N-hydroxysuccinimide followed by 140 mg of 1-ethyl-3-(3-dimethylaminopropyl)carbodiimide HCl and stirred at room temp. overnight. The mixture was diluted with 10 mL of $CH_2Cl_2$, washed with 10 mL of 0.1 N HCl, 10 mL of sat. brine, 2×10 mL of sat. $NaHCO_3$, 10 mL of sat. brine, dried over $Na_2SO_4$ and conc. at reduced pressure to a white amorphous solid. This was chromatographed on 80 g of silica gel using EtOAc as eluent to yield 190 mg of 34 as a white amorphous solid.

Synthesis of N-ethylamphetamine Immunogen 26 (Q=KLH 26a)

A solution of 342 mg of purified KLH in 10 mL of 50 mM KPi pH 7.5 was cooled with an ice bath and treated with 4 mL of DMSO added dropwise. 1.7 mL was removed, which was used as a reference. This left 300 mg of KLH in solution. This was then treated with a solution of 50 mg of 24 in 1.0 mL of DMSO added dropwise. The reaction was stirred at room temp. overnight. The reaction and the reference sample were placed in separate 10,000 MW cut-off dialysis tubing (SpectraPor 7) and dialyzed in 1 liter of 33% DMSO-50 mM KPi pH 7.5 at room temp., 3 changes, at least 3 hrs. each, the last one going overnight. This was then dialyzed using a step-down gradient in 1 liter of 20% DMSO, 1 liter of 10% DMSO, 1 liter of 100% KPi pH 7.5 at room temp. at least 3 hrs. each. The bags were then placed in 1 liter of 50 mM $K_2CO_3$ (pH 11.4) and dialyzed for 4 days at 40° C. (changed once on day 2). This was then dialyzed in 1 liter of 50 mM KPi pH 7.5 at 4° C., 6 changes at least 6 hrs. each. Coomassie Blue Protein assay (modified Bradford assay) (Biorad Chem. Co.) gives a protein conc. of 8.16 mg/mL. Trinitrobenzenesulfonic acid (TNBS) assay on a protected sample gives 41.4% of available lysines modified.

Synthesis of N-ethylamphetamine Conjugate 26 (Q=BSA; 26b)

A solution of 500 mL of bovine serum albumin (BSA) (Cohn Fraction V modified powder; Intergen Company, Purchase, N.Y., USA) in 8 mL of 50 mM KPi pH 7.5 was cooled with an ice bath and treated with 11 mL of DMSO added slowly dropwise. This was then treated with a solution of 6.7 mg of 24 in 1 mL of DMSO added dropwise and stirred at room temp. overnight. The mixture was placed into 10,000 MW cut-off dialysis tubing (SpectraPor 7) and dialyzed in 1 liter of 60% DMSO-50 mM KPi pH 7.5 at room temp. 3 changes at least 3 hrs. each, the last one going overnight. This was then dialyzed using a step-down gradient in 1 liter of 40% DMSO, 1 liter of 20% DMSO 1 liter of 10% DMSO and 1 liter of 100% 50 mM KPi pH 7.5 at room temp. at least 3 hrs. each. This was then dialyzed in 1 liter of 50 mM $K_2CO_3$ (adjusted to pH 13 with KOH) for 4 days with 4 changes of buffer. This was then dialyzed in 1 liter of 50 mM KPi pH 7.5 at 4° C., 6 changes, at least 6 hrs. each. Coomassie Blue Protein Assay gives a protein conc. of 12.2 mg/mL.

Development of Hybridomas to Ecstasy Drugs Using MDMA-Immunogen

Immunizations:

BALB/c female mice of 18–24 weeks of age were immunized with 12 (T=KLH; 12a). The immunogen was emulsified in Freund's Adjuvant and administered via intraperitoneal (IP) injection. Injections were given at no less than 21 day intervals, and typically comprised 50 μg of the conjugate in 100 μL of 50% saline, 50% Adjuvant emulsion. Complete Freund's Adjuvant was used for the primary immunization, and Incomplete Freund's Adjuvant used thereafter. A booster immunization of 50 μg in the same emulsion was administered IP 4 days prior to fusion.

Fusion:

On the day of performing the fusion the mouse was killed by cervical dislocation and a blood sample taken. The spleen and popliteal, inguinal, subclavial and deep inguinal lymph nodes were harvested and pooled. These were ground between two sterile glass slides to release the lymphocytes. One-half of the resulting lymphocyte suspension was used to fuse with the FO myeloma cell line, the remaining half was fused with the P3 myeloma (both myelomas were from ATCC).

Fusion consisted with adding myeloma cells (⅕ the number of lymphocytes), washing via centrifugation, resuspension in serum-free warm Iscove's Modified Dulbecco's Media, and re-centrifugation. The centrifuge tubes containing the resulting pellets were gently tapped to loosen the cells, then 1 mL of warmed PEG/DMSO solution (Sigma Chemical Co.) was slowly added with gentle mixing. The cells were kept warm for 1.5 minutes, after which pre-warmed serum-free IMDM was added at the following rates: 1 mL/min, 2 mL/min, 4 mL/min, 10 mL/min, then the tube was filled to 50 mL, sealed and incubated for 15 minutes. The cell suspensions were centrifuged, the supernatant decanted, and IMDM containing 10% Fetal calf serum was added. The cells were centrifuged once again, and re-suspended in complete cloning medium. This consists of IMDM, 10% FCS, 10% Condimed H1 (Roche Molecular Systems, Pleasanton, Calif., USA), 4 mM Glutamine, 50 μM 2-mercaptoethanol, 40 μM ethanolamine, and pen/strep antibiotics. The cells were suspended at a density of $4\times10^5$ lymphocytes/mL, distributed 100 μl/well into sterile 96-well sterile microculture plates and incubated at 37° C. in 5% carbon dioxide for 24 hours. The next day, 100 μL of HMT selective medium (Cloning medium+1:25 HMT supplement from Sigma Chemical Co.) was added. On the $6^{th}$ day of incubation, approximately 150 μL of media was drawn from each well using a sterile 8-place manifold connected to a light vacuum source. One hundred fifty microliters of HT media was then added. This consists of Cloning Medium+ 1:50 HT supplement (Sigma Chemicals). The plates were returned to the incubator and inspected daily for signs of growth. When growth was judged sufficient, wells were screened for antibody production via ELISA.

ELISA Screening:

Microplates were coated with 100 µL methylenedioxymethamphetamine-BSA conjugate 12 (T=BSA; 12b) at a concentration of 1 mg/mL and separate plates with either 100 µL methamphetamine-BSA (MAMP-BSA) 28 at a concentration of 1 mg/mL

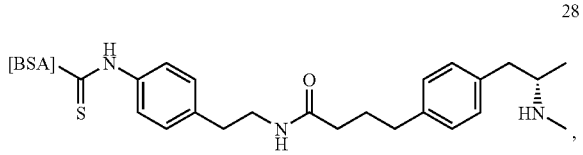

or with 100 µL of Amphetamine-BSA (AMP-BSA) 30 at a concentration of 1 mg/mL

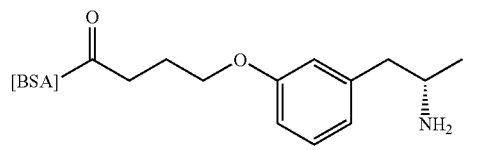

All dilutions are in 0.1 M carbonate buffer pH 9.5.

The plates were incubated covered for 1 hour at 37° C. (humidified). The plates were then emptied and filled with a post-coat solution consisting of Tris buffer, 1% gelatin hydrolysate, 2% sucrose, and 0.17% Tween-20 (all reagents were from Sigma Chemical Co.). The plates were incubated covered for an additional 1 hour at 37° C. (humidified) after which they were washed with Phosphate-buffered Saline containing 0.1% Tween 20. The plates were then filled with a 2% sucrose solution in 0.15M Tris, pH 7.2–7.4 briefly, then emptied and allowed to air dry at room temperature. When dried, the plates were packed in zip-lock bags containing several desiccant pillows, sealed and stored at 4° C. until use.

Primary Fusion Screen.

For the primary screening of the growing clones from the fusion plates, only the MDMA-BSA (12; T=BSA, 12b) coated plates were used. Fifty microliters of PBS was added to each well, followed by 50 µL of the sample of culture media from wells on the fusion plate, diluted 1:10 in PBS. The plates are incubated covered for 1 hour at 37° C., then washed with PBS-Tween (0.1%). The wells are then filled with 100 µL of goat anti-mouse IgG-HRP conjugate (Zymed Labs) diluted in PBS-Tween and the plates re-incubated for 1 hour. The plates are then washed again, and 100 µL of K-Blue substrate (Neogen Corp) added. This is allowed to develop for 5–15 minutes, the reaction being stopped by the addition of 100 µL of 1 N HCl. Color is read by means of a microplate reader at 450 nm and collected by computer for analysis. Those wells that showed the presence of antibody binding to MDMA-BSA (12; T=BSA, 12b) were selected for further processing. Cells were subjected to limiting dilution subcloning, and upon appearance of growth, were tested by a secondary screen.

Secondary Screen.

Four plates coated with the MDMA-BSA conjugate (12; T=BSA, 12b) are prepared by adding 50 µL of Phosphate buffered saline (PBS) to the wells of one plate, 50 µL of a solution of free MDMA (800 ng/mL) to the second plate, 50 µL of a solution of MDEA (800 ng/mL) to the third plate, and 50 µL of a solution of pseudoephedrine (8 µg/mL) to the fourth plate. All drugs were dissolved in PBS. Fifty microliters of PBS are added to the wells of the MAMP-BSA (28) and AMP-BSA (30) coated plates.

When the growing subclones were judged ready for testing, 25 µL of supernatant from the wells were taken and transferred to 96-well flexible plates. Culture medium is added to each well to provide a 1:10 dilution of the media sample. Fifty microliters of the diluted sample are transferred to each of the coated plates above. Subsequent processing was exactly as for the Primary screen. Criteria for selection were binding to the MDMA-BSA (Methylenedioxymethamphetamine-BSA) conjugate (12; T=BSA, 12b), and indication of inhibition by free MDMA and/or MDEA, and little or no inhibition by pseudoephedrine. Binding to the AMP-BSA (30) and MAMP-BSA conjugates (28) was for reference only.

Clones chosen were immediately subcloned, and when ready, retested by the secondary screen procedure. Stable subclones were expanded, frozen and the spent media used to determine specificity using the Cross-reactivity Assay. Subclones are identified by adding a "." suffix and a number indicating the order of selection, to the parent clone designation.

Table 4 presents a portion of the screening results.

TABLE 4

| Clone | MDMA-BSA (12b) plates | | | | (30) plates | (28) plates |
|---|---|---|---|---|---|---|
| | +PBS | +MDMA | +MDEA | +Pseu | | |
| MDMA-2 | 3.169 | — | — | — | — | — |
| MDMA-2.1 | 3.771 | 0.796 | 0.370 | 3.806 | 0.139 | 0.153 |
| MDMA-2.1.1 | 4.200 | 0.857 | 0.754 | 3.910 | 1.679 | 0.089 |
| MDMA-14 | 4.131 | — | — | — | — | — |
| MDMA-14.1 | 3.898 | 0.724 | 0.454 | 3.802 | 0.241 | 0.145 |

Cross-Reactivity Assay

Supernatants are subjected to serial dilutions and re-tested in the ELISA screen above. The dilution providing for about a 50% reduction from the maximum OD is chosen for proceeding to cross-reactivity testing. This consists of repeating the preceding assay with the antibody at the chosen dilution and in the presence of varying concentrations of drugs. The charts shown in FIG. 5 and FIG. 6 present the results of such determinations.

Development of Hybridomas to Ecstasy Drugs using N-Ethylamphetamine Immunogen

Immunizations

SJL female mice of 18–24 weeks of age were immunized via a modified RIMMS method (Kilpatrick et al., *Hybridoma*, 1997, 16:4, pp. 381–389). Briefly, immunogen 26 (Q=KLH, 26a)

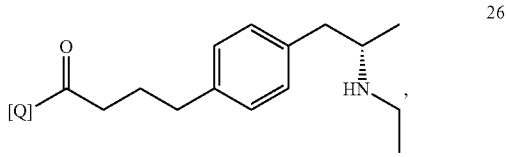

wherein Q is KLH was emulsified in incomplete Freund's Adjuvant and administered via subcutaneous injection at 6 sites distributed over the nape of the neck, and bilaterally to the calf and groin. Injections were given on day 0, day 3, day 6, and day 11. The respective dosages given were: 50 µg, 25 µg, 12 µg, and 6 µg total amounts.

Fusion

On day 13 two mice were killed via exsanguinations. The popliteal, inguinal, subclavial and deep inguinal lymph nodes were harvested and pooled. These nodes were ground between two sterile glass slides to release the lymphocytes. One-half of the resulting lymphocyte suspension was used to fuse with the F0 myeloma cell line. The remaining half was fused with the P3 myeloma (both myelomas were obtained from ATCC).

Fusion consisted of adding myeloma cells (⅕ the number of lymphocytes), washing via centrifugation, resuspension in serum-free warm Iscove's Modified Dulbecco's Media, and re-centrifugation. The centrifuge tubes containing the resulting pellets were gently tapped to loosen the cells, then 1 mL of warmed PEG/DMSO solution (Sigma Chemical Co.) was slowly added with gentle mixing. The cells were kept warm for 1.5 minutes, after which pre-warmed serum-free INMM was added at the following rates: 1 mL/min, 2 mL/min, 4 mL/min, and 10 mL/min. Then, the tube was filled to 50 mL, sealed and incubated for 15 minutes. The cell suspensions were centrifuged, the supernatant decanted, and IMDM containing 10% Fetal calf serum was added. The cells were centrifuged once again, and resuspended in complete cloning medium. This consists of IMDM, 10% FCS, 10% Condimed H1 (Roche Molecular Systems, Pleasanton, Calif., USA), 4 mM Glutamine, 50 µM 2-mercaptoethanol, 40 µM ethanolamine, and pen/strep antibiotics. The cells were suspended at a density of $4 \times 10^5$ lymphocytes/mL, distributed 100 µL/well into sterile 96-well microculture plates, and incubated at 37° C. in 5% $CO_2$ for 24 hours. The next day, 100 µL of HMT selective medium (Cloning medium+1:25 HMT supplement from Sigma Chemicals) was added. On the 6$^{th}$ day of incubation, approximately 150 µL of media was drawn from each well using a sterile 8-place manifold connected to a light vacuum source. One hundred fifty microliters of HT media was then added. This consists of Cloning Medium+1:50 HT supplement (Sigma Chemical Co.). The plates were returned to the incubator and inspected daily for signs of growth. When growth was judged sufficient, wells were screened for antibody production via ELISA.

ELISA Screening

Microplates were coated with 100 µL Methamphetamine-BSA conjugate 28 and separate plates with 100 µL N-ethylamphetamine-BSA 26 (Q=BSA, 26b) at 1 µg/mL in 0.1 M carbonate buffer, pH 9.5 for 1 hour at 37° C. (humidified). The plates were then emptied and filled with a post-coat solution consisting of Tris buffer, 1% gelatin hydrolysate, 2% sucrose, and 0.17% Tween-20 (all reagents were from Sigma Chemical Co.). The plates were incubated for an additional 1 hour at 37° C. (humidified) after which they were washed with Phosphate-buffered Saline containing 0.1% Tween 20. The plates were then filled with a 2% sucrose solution in 0.15 M Tris, pH 7.2–7.4 briefly, then emptied and allowed to air-dry at room temperature. When dried, the plates were packed in zip-lock bags containing several desiccant pillows, sealed and stored at 4° C. until use.

When the growing clones were judged ready for testing, 25 µL of supernatant from the wells were taken and transferred to 96 well flexible plates. Culture medium is added to each well to provide a 1:10 dilution of the media sample. One hundred microliters of the diluted sample are transferred to each of the coated plates above. The plates are incubated covered for 1 hour at 37° C., then washed with PBS-Tween. The wells are then filled with 100 µL of goat anti-mouse IgG-HRP conjugate (Zymed Labs) diluted in PBS-Tween and the plates re-incubated for 1 hour. The plates are then washed again, and 100 µL of K-Blue substrate (Neogen Corp) are added. This is allowed to develop for 5–15 minutes, the reaction being stopped by the addition of 100 µL of 1 N HCl. Color is read by means of a microplate reader at 450 nm and collected by computer for analysis. A criterion for selection was binding to the Methamphetamine-BSA conjugate 28. Table 5 presents binding data for a portion of the screening of the Meth-BSA 28 and NEAMP-BSA 26 (Q=BSA, 26b) coated plates.

TABLE 5

| Clone | Meth-BSA 28 | NEAMP-BSA 26b |
|---|---|---|
| Neamp-1 | 0.539 | 0.356 |
| Neamp-2 | 0.350 | 1.146 |
| Neamp-4 | 1.079 | 1.617 |

Clones chosen were immediately subcloned, and when ready, retested. Stable subclones were expanded, frozen and the spent media used to determine specificity using the Cross-reactivity Assay.

Cross-Reactivity Assay

Supernatants are subjected to serial dilutions and re-tested in the ELISA screen above. The dilution providing for about a 50% reduction from the maximum OD is chosen for proceeding to cross-reactivity testing. This consists of repeating the preceding assay with the antibody at the chosen dilution and in the presence of varying concentrations of drugs. The chart shown in FIG. 7 presents the results of such a determination, while Table 3 (vide supra) shows the percentage cross-reactivity determined.

The foregoing detailed description and examples have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A compound having a structure

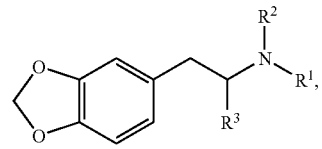

wherein:
$R^1$ is —J—M—T;
$R^2$ is a protecting group; and
$R^3$ is an optionally substituted alkyl group; wherein
  J is a straight or branched chain comprising 1–15 carbon atoms and 0–6 heteroatoms;
  M is —CO—, and
  T is selected from the group consisting of a hydroxyl and a leaving group.

2. The compound of claim 1 wherein J comprises 1–11 carbon atoms.

3. The compound of claim 2 wherein J is —(CH$_2$)$_k$—and k is 1, 2, 3, 4, 5, or 6.

4. The compound of claim 3 wherein R$^3$ is selected from the group consisting of methyl, ethyl, n-propyl, and n-butyl.

5. The compound of claim 4 wherein k is 3.

6. The compound of claim 5 wherein T is a leaving group.

7. The compound of claim 5 wherein R$^2$ is a protecting group, and R$^3$ is methyl.

8. The compound of claim 5 wherein T is a leaving group comprising N-oxysuccinimide.

9. The compound of claim 8 wherein R$^3$ is methyl.

10. The compound of claim 7 wherein R$^2$ is trifluoroacetyl and T is N-oxysuccinimide.

11. The compound of claim 7 wherein R$^2$ is trifluoroacetyl and T is hydroxyl.

12. A compound having a structure

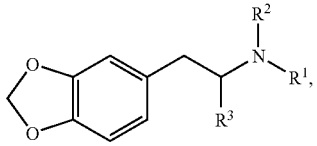

wherein:
R$^1$ is —J—M—T;
R$^2$ is a protecting group; and
R$^3$ is an optionally substituted alkyl group; wherein
    J is a straight or branched chain comprising 1–15 carbon atoms and 0–6 heteroatoms;
    M is selected from the group consisting of —O—, —CO—, —NR$^4$—, —S—, —C(=NH)O—, —NH(CO)—, —NH(CO)NH—, —NH(CS)—, —NH(CS)NH—, —O(CO)NH—, and —NH(C=NH)—, wherein R$^4$ is selected from the group consisting of hydrogen and an alkyl group; and
T is a macromolecular carrier.

13. The compound of claim 12 wherein J is a straight chain comprising 3 carbon atoms and M is —CO—.

14. The compound of claim 12 wherein the macromolecular carrier is selected from the group consisting of a protein, a polypeptide, and a polysaccharide.

15. The compound of claim 14 wherein the protein is selected from the group consisting of keyhole limpet hemocyanin, bovine serum albumin, and bovine thyroglobulin.

16. The compound of claim 12 wherein T is a macromolecular carrier selected from the group consisting of a hemocyanin, a globulin, and an albumin.

17. The compound of claim 16 wherein R$^3$ is methyl.

18. A compound having a structure

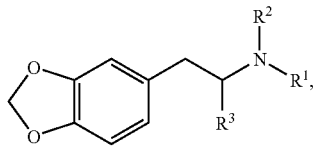

wherein:
R$^1$ is —J—M—T;
R$^2$ is a protecting group; and
R$^3$ is an optionally substituted alkyl group; wherein
    J is a straight or branched chain comprising 1–15 carbon atoms and 0–6 heteroatoms;
    M is selected from the group consisting of —O—, —CO—, —NR$^4$—, —S—, —C(=NH)O—, —NH(CO)—, —NH(CO)NH—, —NH(CS)—, —NH(CS)NH—, —O(CO)NH—, and —NH(C=NH)—, wherein R$^4$ is selected from the group consisting of hydrogen and an alkyl group; and
T is a label.

* * * * *